US006316257B1

(12) United States Patent
Flyer et al.

(10) Patent No.: US 6,316,257 B1
(45) Date of Patent: Nov. 13, 2001

(54) MODIFIED RAPID EXPANSION METHODS ("MODIFIED-REM") FOR IN VITRO PROPAGATION OF T LYMPHOCYTES

(75) Inventors: David C. Flyer, Redmond; Kim W. Clary, Seattle, both of WA (US)

(73) Assignee: Targeted Genetics Corporation, Seattle, WA (US)

( * ) Notice: Subject to any disclaimer, the term of this patent is extended or adjusted under 35 U.S.C. 154(b) by 0 days.

(21) Appl. No.: 08/793,707

(22) PCT Filed: Mar. 3, 1997

(86) PCT No.: PCT/US97/03293

§ 371 Date: Mar. 3, 1997

§ 102(e) Date: Mar. 3, 1997

(87) PCT Pub. No.: WO97/32970

PCT Pub. Date: Sep. 12, 1997

Related U.S. Application Data

(60) Provisional application No. 60/037,333, filed on Mar. 4, 1996.

(51) Int. Cl.[7] .............................. C12N 5/08; C12N 5/16; C12N 5/00; C07K 16/00
(52) U.S. Cl. ................... 435/372.3; 435/325; 435/343.2; 435/372; 435/373; 435/375; 435/383; 435/384; 435/386; 530/351; 530/388; 530/389
(58) Field of Search ............................... 435/325, 343.2, 435/344, 366, 372, 372.3, 373, 375, 383, 384, 386; 530/351, 388, 389

(56) References Cited

U.S. PATENT DOCUMENTS

| | | | |
|---|---|---|---|
| 4,544,632 | 10/1985 | Yamamura et al. | 435/70.2 |
| 4,675,291 | 6/1987 | Yamamura et al. | 435/70.3 |
| 4,839,290 | 6/1989 | Kaieda et al. | 435/70.3 |
| 5,057,423 | 10/1991 | Hiserodt et al. | 435/5 |
| 5,399,346 | 3/1995 | Anderson et al. | 424/93.21 |
| 5,827,642 | 10/1998 | Riddell et al. | 435/2 |
| 5,858,358 * | 6/1994 | June et al. | 424/130.1 |

FOREIGN PATENT DOCUMENTS

| | | |
|---|---|---|
| 4410136 | 1/1994 | (DE) . |
| 0440373 | 8/1991 | (EP) . |
| WO 88/07077 | 9/1988 | (WO) . |
| WO 92/05794 | 4/1992 | (WO) . |
| WO 92/08796 | 5/1992 | (WO) . |
| WO 96/06929 | 3/1996 | (WO) . |

OTHER PUBLICATIONS

Boehme, S.A., Lenardo, M.J., "Propriocidal apoptosis of mature T lymphocytes occurs at S phase of the cell cycle", (1993), *European Journal of Immunology*, 23:1552–1560.

Burgess et al., "The Nature and Action of Granulocyte–Macrophage Colony Stimulating Factors", (1980), *Blood*, 56:947–958.

Ciavarra et al., "Analysis of T–Cell Subset Proliferation at Afebrile and Febrile Temperatures: Differential Response of Lyt–1+23– Lymphocytes to Hyperthermia following Mitogen and Antigen Stimulation and Its Functional Consequence on Development of Cytotoxic Lymphocytes", (1987), *Cellular Immunology*, 107:293–306.

Crossland et al., "T Cells from Tumor–Immune Mice Non-specifically Expanded in Vitro witih Anti–CD3 plus IL–2 Retain Specific Function in Vitro and can Eradicate Disseminated Leukemia in Vivo", (1991), *Journal of Immunology*, 146:4414–4420.

Emmrich et al., "Synergism in the activation of human CD8 T cells by cross–linking the T–cell receptor complex with the CD8 differentiation antigen" (1986), *Proc. Natl. Acad. Sci. USA*, 83:8298–8302.

Gantner et al., "Concanavalin A—Induced T–Cell—Mediated Hepatic Injury in Mice: The Role of Tumor Necrosis FActor", (1995), *Hepatology*, 21:190–198.

Geppert et al., "Accessory Cell Signals Involved in T–Cell Activation", (1990), *Immunology Reviews*, 117:5–66.

Gilbert et al., "Selective Interference with Class I Major Histocompatibility Complex Presentation of the Major Immediate–Early Protein following Infection with Human Cytomegalovirus", (1993), *Journal of Virology*, 67:3461–3469.

Gillis, S., Interleukin–2 Dependent Culture of Cytolytic T Cell Lines, (1981), *Immunology Review*, 54:81–109.

Greenberg, "Adoptive T Cell Therapy of Tumors: Mechanisms Operative in the Recognition and Elimination of Tumor Cells", (1991), *Advances in Immunology*, 49:281–355.

Heeg et al., "Clonal Specifity Analysis of Mitogen–Activated Murine T Lymphoblasts", (1987), *Immunobiology*, 175:431–446.

Ho et al., A Phase 1 Study of Adoptive Transfer of Autologous CD8+ T Lymphocytes in Patients With aCquired Immunodeficiency Syndrome (AIDS)–Related Complex or AIDS, (1993), *Blood*, 81:2093–2101.

Kobayashi et al., "Identification and Purification of Natural Killer Cell Stimulatory Factor (NKSF), A Cytokine with Multiple Biologic Effects on Human Lymphocytes", (1989), *Journal of Exp. Med.*, 170:827–845.

(List continued on next page.)

Primary Examiner—David Guzo
Assistant Examiner—Gerald G. Leffers, Jr.
(74) Attorney, Agent, or Firm—Morrison & Foerster LLP

(57) ABSTRACT

The present invention provides a modified rapid expansion method (termed "low-PBMC-REM" or "modified-REM"), for quickly generating large numbers of T lymphocytes, including cytolytic and helper T lymphocytes, without using the large excesses of peripheral blood mononuclear cells (PBMC) or EBV-transformed lymphoblastoid cells (LCL) characteristic of high-PBMC-REM. Clonal expansions of greater than 500-fold can be achieved within a single stimulation cycle of about 8–14 days.

26 Claims, No Drawings

OTHER PUBLICATIONS

Lamb–Wharton et al., "Induction of T–Lymphocyte Adhesion by Histidine–Proline–Rich Glycoprotein and Concanavalin A", (1993), *Cellular Immunology*, 152:544–555.

Lenardo, M.J., "Interleukin–2 programs mouse $\alpha\beta$ T lymphocytes for apoptosis", (1991), *Nature*, 353:858–861.

Liu et al., "Epstein–Barr Virus–Transformed Lymphoblastoid Cell Lines as Antigen–Presenting Cells and "Augmenting" Cells for Human CMV–Specific $T_h$ Clones", (1987), *Cellular Immunology*, 108:64–75.

Mazumder et al., "Phase I Study of the Adoptive Immunotherapy of Human Cancer With Lectin Activated Autologous Mononuclear Cells", (1984), *Cancer*, 53:896–905.

Miller, A.D., "Retroviral Vectors", *Current Topics in Microbiology and Immunology*, 158:1–24.

Miller et al., "Differential Sensitivity of Virgin and Memory T Lymphocytes to Calcium Ionophores Suggests a Buoyant Density Separation Method and a Model for Memory Cell Hyporesponsiveness to Con A", (1991), *Journal of Immunology*, 147:3080–3086.

Moore et al., "Culture of Normal Human Leukocytes", (1967), *J. Am. Med. Assoc.*, 199:87–92.*

Morecki et al., "Retrovirus–mediated gene transfer into CD4+ and CD8+ human T cell subsets derived from tumor-infiltrating lymphocytes and peripheral blood mononuclear cells", (1991), *Cancer Immunol. Immunother*, 32:342–352.*

Nagi et al., "Concanavalin A–induced suppressor cell activity in intestinal mucosal leukocytes obtained from healthy cows", (1989), *American Journal of Veterinary Research*, 50:1266–1271.*

Owens et al., "Coaggregation of the T–cell receptor with CD4 and other T–cell surface molecules enhances T–cell activation", (1987), *Proc. Natl. Acad. Sci. USA*, 84:9209–9213.*

Paul et al., "Long–term growth and cloning of non–transformed lymphocytes", (1981), *Nature*, 294:697–699.*

Peltz et al., "Cloned and Expressed Human Fe Receptor for IgG Mediates Anti–CD3–Dependent Lymphoproliferation", (1988), *Journal of Immunology*, 141:1891–1896.*

Ravetch and Kinet, "Fc Receptors", (1991), *Annual Review of Immunology*, 9:457–492.*

Reusser et al., "Cytotoxic T–Lymphocyte Response to Cytomegalovirus After Human Allogenic Bone Marrow Transplantation: Pattern of Recovery and Correlation With Cytomegalovirus Infection and Disease", (1991), *Blood*, 78:1373–1380.*

Riddell and Greenberg, "The use of anti–CD3 and anti–CD28 monoclonal antibodies to clone and expand human antigen–specific T cells", (1990), *Journal of Immunology Methods*, 128:189–201.*

Riddell et al., "Phase 1 Study of Cellular Adoptive Immunotherapy Using Genetically Modified CD8+ HIV–Specific T Cells for HIV Seropositive Patients Undergoing Allogeneic Bone Marrow Transplant", (1992), *Human Gene Therapy*, 3:319–338.*

Riddell et al., "Class 1 MHC–Restricted Cytotoxic T Lymphocyte Recognition of Cells Infected with Human Cytomagalovirus Does Not Require Endogenous Viral Gene Expression", (1991), *Journal of Immunology*, 146:2795–2804.*

Riddell et al., "Restoration of Viral Immunity in Immunodeficient Humans by the Adoptive Transfer of T Cell Clones", (1992), *Science*, 257:238–241.*

Roe et al., "Integration of Mouse Leukemia Virus DNA Depends on Mitosis", (1993), *EMBO Journal*, 12:2099–2108.*

Rosenberg et al., "A Progress Report on the Treatment of 157 Patients With Advanced Cancer Using Lymphokine-–Activated Killer Cells and Interleukin–2 or High–Dose Interleukin–2 Alone", (1987), *New England Journal of Medicine*, 316:889–897.*

Rosenberg et al., "Gene Transfer Into Humans—Immunotherapy of Patients With Advanced Melanoma, Using Tumor–Infiltrating Lymphocytes Modified by Retroviral Gene Transduction", (1990), *New England Journal of Medicine*, 323:570–578.*

Rosenberg et al., "A New Approach to the Adoptive Immunotherapy of Cancer with Tumor–Infiltrating Lymphocytes", (1986), *Science* 233:1318–1321.

Rosenberg, "Use of Tumor–Infiltration Lymphocytes and Interleukin–2 in the Immunotherapy of Patients with Metastatic Melanoma", (1988), *New England Journal of Medicine*, 319:1676–1680.

Saizawa et al., "Evidence for a physical association of CD4 and the CD3:$\alpha$:$\beta$ T–cell receptor", (1987), *Nature*, 328:260–263.

Sakai et al., "Dissociation of interleukin–2 production from the cell activation in response to the mitogenic lectin in peripheral CD4+ T cells of LEC mutant rats", (1993), *Immunology*, 79:491–497.

Sakai et al., "Expression of Major Histocompatibility Complex Class II but Not of CD8 Molecules by Lectin–Stimulated Peripheral CD4+ T Cells in LEC Mutant Rats", (1994), *Cellular Immunology*, 158:414–422.

Schook et al, "Lymphokine and Monokine Activities in Supernatants from Human Lymphoid and Myeloid Cell Lines", (1981), *Lymphokines*, 2:1–19.

Semnani et al., "Costimulation by Purified Intercellular Adhesion Molecule 1 and Lymphocyte Function–associated Antigen 3 Induces Distinct Proliferation, Cytokine and Cell Surface Antigen Profiles in Human 'Naïve' and 'Memory' CD4+ T Cells", (1994), *Journal of Exp. Med.*, 180:2125–2135.

Springett et al., "Infection Efficiency of t Lymphocytes with Amphotropic Retrovirus Vectors Is Cell Cycle Dependent", (1989), *Journal of Virology*, 63:3865–3869.

Tiberghein et al., "Ganciclovir Treatment of Herpes Simplex Thymidine Kinase–Transduced Primary T Lymphocytes: An Approach for Specific In Vivo Donor T–Cell Depletion After Bone Marrow Transplantation?", (1994), *Blood*, 84(4);1333–1341.

Tiegs et al., "A T–Cell–dependent Experimental Liver Injyry in Mice Inducible by Concanavalin A", (1992), *Journal of Clinical Investigation*, 90:196–203.

Van de Griend et al., "Rapid Expansion of Human Cytotoxic T Cell Clones: Growth Promotion by a Heat–Labile Serum Component and by Various Types of Feeder Cells", (1984), *Journal of Immunology Methods*, 66:285–298.

Van de Griend et al., "Rapid Expansion of Allospecific Cytotoxic T Cell Clones Using Non–Specific Feeder Cell Lilnes Without Further Addition of Exogenous ILl2", (1984), *Transplantation*, 38:401–406.

Weaver et al., "Syngeneic Transplantation With Peripheral Blood Mononuclear Cells Collected After the Administration of Recombinant Human Granulocyte Colon–Stimulating Factor", (1993), *Blood*, 82:1981–1984.

Weber et al., "Activation Through CD3 Molecule Leads to Clonal Expansion of All Human Peripheral Blood T Lymphocytes: Functional Analysis of Clonally Expanded Cells", (1985), *Journal of Immunology*, 135: 2337–2342.

Yang et al., "Expression of HLA–DR Antigen in Human Class II Mutant B–Cell Lines by Double Infection with Retrovirus Vectors", (1987), *Mol. Cell Biol.*, 7(11):3923–3928.

Greenberg, P. D. et al. (1991). "Development of a Treatment Regimen for Human Cytomegalovirus (CMV) Infection in Bone Marrow Transplantation Recipients by Adoptive Transfer of Donor–Derived CMV–Specific T Cell Clones Expanded In Vitro," *Ann. NY Acad. Sci.* 636:184–195.

Lupton, S. D. et al. (1991). "Dominant Positive and Negative Selection Using a Hygromycin Phosphotransferase–Thymidine Kinase Fusion Gene," *Mol. Cell. Biol.* 11(6):3374–3378.

Miescher, S. et al. (1987). "Clonal and Frequency Analyses of Tumor–Infiltrating T Lymphocytes from Human Solid Tumors," *J. Immunol.* 138(11):4004–4011.

Mor, F. et al. (1990). "Clinical Modeling of T Cell Vaccination Against Autoimmune Disease in Rats: Selection of Antigen–Specific T Cells Using a Mitogen," *J. Clin. Invest.* 85(5):1594–1598.

* cited by examiner

MODIFIED RAPID EXPANSION METHODS ("MODIFIED-REM") FOR IN VITRO PROPAGATION OF T LYMPHOCYTES

This application is a national phase filing under 35 USC § 371 of International Patent Application No. PCT/US97/03293, filed Mar. 3, 1997, which claims priority to U.S. Provisional Application No. 60/037,333, which was converted from U.S. patent application Ser. No. 08/610,710, filed Mar. 4, 1996.

FIELD OF THE INVENTION

This invention relates to improved methods for culturing T lymphocytes, including human antigen-specific cytolytic and helper T lymphocytes. The methods of the present invention result in the very rapid and efficient expansion of T cells which are useful, for example, in cellular immunotherapy.

BACKGROUND

T lymphocytes are formed in the bone marrow, migrate to and mature in the thymus and then enter the peripheral blood and lymphatic circulation. T lymphocytes can be phenotypically subdivided into several distinct types of cells including: helper T cells, suppressor T cells, and cytotoxic T cells. T lymphocytes, unlike B lymphocytes, do not produce antibody molecules, but express a heterodimeric cell surface receptor that can recognize peptide fragments of antigenic proteins that are attached to proteins of the major histocompatibility complex (MHC) expressed on the surfaces of target cells; see, e.g., Abbas, A. K., Lichtman, A. H., and Pober, J. S., *Cellular and Molecular Immunology*, 1991, esp. pages 15–16.

T lymphocytes that can be expanded according to the present invention are of particular interest in the context of cellular "immunotherapy". As used herein, cellular immunotherapy refers to any of a variety of techniques involving the introduction of cells of the immune system, especially T lymphocytes, into a patient to achieve a therapeutic benefit. Such techniques can include, by way of illustration, "immuno-restorative" techniques (involving, e.g., the administration of T cells to a patient having a compromised immune system); "immuno-enhancing" techniques (involving, e.g., the administration of T cells to a patient in order to enhance the ability of that patient's immune system to avoid or combat a cancer or a pathogen such as a virus or bacterial pathogen); and "immuno-modulating" techniques (involving, e.g., the administration of T cells to a patient in order to modulate the activity of other cells of the patient's immune system, such as in a patient affected by an autoimmune condition).

Cytotoxic T lymphocytes (CTLs) are typically of the CD3+, CD4−, CD8+ phenotype and lyse cells that display fragments of foreign antigens associated with class I MHC molecules on their cell surfaces. CTLs that are CD3+, CD4+, CD8− have also been identified. Target cells for CTL recognition include normal cells expressing antigens after infection by viruses or other pathogens; and tumor cells that have undergone transformation and are expressing mutated proteins or are over-expressing normal proteins.

Most "helper" T cells are CD3+, CD4+, CD8−. Helper T cells recognize fragments of antigens presented in association with class II MHC molecules, and primarily function to produce cytokines that amplify antigen-specific T and B cell responses and activate accessory immune cells such as monocytes or macrophages. See, e.g., Abbas, A. K., et al., supra. Helper T cells can also participate in and/or augment cytolytic activites.

In addition to conventional helper T cells and cytolytic or "killer" T cells, it will also be useful to be able to rapidly expand other T cell populations. For example, T cells expressing the gamma/delta T cell receptor represent a relatively small portion of the human T cell population, but are suspected to play a role in reactivity to viral and bacterial pathogens as well as to tumor cells (see, e.g., W. Haas et al. 1993. Annu. Rev. Immunol. 11:637). Another T cell population of potential clinical importance is the population of CD1-restricted T cells. CD1 is an MHC-like molecule that shows limited polymorphism and, unlike classical MHC molecules which "present" antigenic peptides, CD molecules bind lipoglycans and appear to be important in the recognition of microbial antigens (see, e.g., P. A. Sieling et al. 1995. Science 269:227; and E. M. Beckman et al. 1994. Nature 372:691).

T lymphocytes are thus key components of the host immune response to viruses, bacterial pathogens and to tumors. The significance of properly functioning T cells is made quite clear by individuals with congenital, acquired or iatrogenic T cell immunodeficiency conditions (e.g., SCID, BMT, AIDS, etc.) which can result in the development of a wide variety of life-threatening infections or malignancies. Persons with diseases that are related to a deficiency of immunologically-competent T lymphocytes, or persons with conditions that can be improved by administering additional T lymphocytes, can thus be benefited by cellular immunotherapies, as referred to above. T cells for use in such therapies can be derived from the immunodeficient host, or from another source (preferably a compatible donor). The latter source is of course especially important in situations in which an immunodeficient host has an insufficient number of T cells, or has T cells that are insufficiently effective. In either case, it is difficult to obtain sufficient numbers of T cells for effective administration; and thus target T cells must first be grown to large numbers in vitro before administration to a host.

After undergoing such cellular immunotherapy, hosts that previously exhibited, e.g., inadequate or absent responses to antigens expressed by pathogens or tumors, can express sufficient immune responses to become resistant or immune to the pathogen or tumor.

Adoptive transfer of antigen-specific T cells to establish immunity has been demonstrated to be an effective therapy for viral infections and tumors in animal models (reviewed in Greenberg, P. D., *Advances in Immunology* (1992)). For adoptive immunotherapy to be effective, antigen-specific T cells usually need to be isolated and expanded in numbers by in vitro culture, and following adoptive transfer such cultured T cells must persist and function in vivo. For treatment of some human diseases, the use in immunotherapy of cloned antigen-specific T cells which represent the progeny of single cells, offers significant advantages because the specificity and function of these cells can be rigorously defined and precise dose:response effects readily evaluated. Riddell et al. were the first to adoptively transfer human antigen-specific T cell clones to restore deficient immunity in humans. Riddell, S. R. et al., "Restoration of Viral Immunity in Immunodeficient Humans by the Adoptive Transfer of T Cell Clones", *Science* 257:238–240 (1992). In that study, Riddell et al. used adoptive immunotherapy to restore deficient immunity to cytomegalovirus in allogeneic bone marrow transplant recipients. Cytomegalovirus-specific CD8+ cytotoxic T cell clones were isolated from three CMV seropositive bone marrow donors, propagated in vitro for 5 to 12 weeks to achieve numerical expansion of effector T cells, and then administered intravenously to the respective bone marrow transplant (BMT) recipients. The BMT recipients were deficient in CMV-specific immunity due to ablation of host T cell responses by the pre-transplant chemoradiotherapy and the delay in recovery of donor immunity commonly observed after allogeneic bone marrow transplant (Reusser et al. *Blood,* 78:1373–1380, 1991). Riddell et al. found that no toxicity was encountered and that the transferred T cell clones provided these immunodeficient hosts with rapid and persistent reconstitution of CD8+ cytomegalovirus-specific CTL responses.

Riddell et al. (*J. Immunology,* 146:2795–2804, 1991) used the following procedure for isolating and culturing the CD8+ CMV-specific T cell clones: peripheral blood mononuclear cells (PBMCs) derived from the bone marrow donor were first cultured with autologous cytomegalovirus-infected fibroblasts to activate CMV-specific CTL precursors. Cultured T cells were then restimulated with CMV-infected fibroblasts and the cultures supplemented with γ-irradiated PBMCs. 2–5 U/ml of interleukin-2 (IL-2) in suitable culture media was added on days 2 and 4 after restimulation to promote expansion of CD8+ CTL (Riddell et al., *J. Immunol.,* 146:2795–2804, 1991). To isolate T cell clones, the polyclonal CD8+ CMV-specific T cells were plated at limiting dilution (0.3–0.6 cells/well) in 96-well round bottom wells with either CMV-infected fibroblasts as antigen-presenting cells (Riddell, *J. Immunol.,* 146:2795–2804, 1991); or anti-CD3 monoclonal antibody to mimic the stimulus provided by antigen-presenting cells. (Riddell, *J. Imm. Methods,* 128:189–201, 1990). Then, γ-irradiated peripheral blood mononuclear cells (PBMC) and EBV-transformed lymphoblastoid cells (LCL) were added to the microwells as feeder cells. Wells positive for clonal T cell growth were evident in 10–14 days. The clonally derived cells were then propagated to large numbers initially in 48- or 24-well plates and subsequently in 12-well plates or 75-cm$^2$ tissue culture flasks. T cell growth was promoted by restimulation every 7–10 days with autologous CMV-infected fibroblasts and γ-irradiated feeder cells consisting of PBMC and LCL, and the addition of 25–50 U/ml of IL-2 at 2 and 4 days after restimulation.

A major problem that exists in the studies described above, and in general in the prior art of culturing T cells, is the inability to grow large quantities of human antigen-specific T cell clones in a timely fashion. It is not known if the slow growth of T cells in culture represents an inherent property of the cell cycle time for human lymphocytes or the culture conditions used. For example, with the culture method used in the CMV adoptive immunotherapy study described above, three months were required to grow T cells to achieve the highest cell dose under study which was $1 \times 10^9$ T cells/cm$^2$. This greatly limits the application of adoptive immunotherapy for human viral diseases and cancer since the disease process may progress during the long interval required to isolate and grow the specific T cells to be used in therapy. Based on extrapolation from animal model studies (reviewed in Greenberg, P. D., Advances in Immunology, 1992), it is predicted that in humans doses of antigen-specific T cells in the range of $10^9$–$10^{10}$ cells may be required to augment immune responses for therapeutic benefit.

However, rapidly expanding antigen-specific human T cells in culture to achieve such high cell numbers has proven to be a significant obstacle. Thus, with the exception of the study by Riddell et al., supra, (in which several months were taken to grow a sufficient number of cells) studies of adoptive immunotherapy using antigen-specific T cell clones have not been performed. The problem of producing large numbers of cells for adoptive immunotherapy was identified in U.S. Pat. No. 5,057,423. In this patent, a method for isolating pure large granular lymphocytes and a method for the expansion and conversion of these large granular lymphocytes into lymphokine activated killer (LAK) cells is described. The methods are described as providing high levels of expansion, i.e. up to 100-fold in 3–4 days of culture. Although LAK cells will lyse some types of tumor cells, they do not share with MHC-restricted T cells the properties of recognizing defined antigens and they do not provide immunologic memory. Moreover, the methods used to expand LAK cells, which predominantly rely on high concentrations of IL-2 do not efficiently expand antigen-specific human T cells (Riddell et al., unpublished); and those methods can render T cells subject to programmed cell death (i.e. apoptosis) upon withdrawal of IL-2 or subsequent stimulation via the T cell receptor (see the discussion of the papers by Lenardo et al, and Boehme et al., infra). Earlier methods that relied on the use of lectins, such as concanavalin A or phytohemagglutinin (see, e.g., Van de Griend et al., *Transplantation* 38: 401–406 (1984), and Van de Griend et al., *J. Immunol. Methods* 66: 285–298 (1984)), are even less satisfactory because the use of such non-specific stimultory lectins tends to induce a number of phenotypic changes in the stimulated cells that make them quite different from T cells stimulated via the CD3 receptor.

The inability to culture antigen-specific T cell clones to large numbers has in part been responsible for limiting adoptive immunotherapy studies for human diseases such as cancer (Rosenberg, *New Engl. J. Med.,* 316:1310–1321, 1986; Rosenberg, *New Engl. J. Med.,* 319:1676–1680, 1988) and HIV infection (Ho M. et al., *Blood* 81:2093–2101, 1993) to the evaluation of activated polyclonal lymphocyte populations with poorly defined antigen specificities. In such studies, polyclonal populations of lymphocytes are either isolated from the blood or the tumor filtrate and cultured in high concentrations of the T cell growth factor IL-2. In general, these cells have exhibited little if any MHC-restricted specificity for the pathogen or tumor and in the minority of patients that have experienced therapeutic benefit, it has been difficult to discern the effector mechanism involved. Typically, adoptive immunotherapy studies with non-specific effector lymphocytes have administered approximately $2 \times 10^{10}$ to $2 \times 10^{11}$ cells to the patient. (See, e.g., U.S. Pat. No. 5,057,423, at column 1, lines 40–43).

The development of efficient cell culture methods to rapidly grow T lymphocytes will be useful in both diagnostic and therapeutic applications. In diagnostic applications, the ability to rapidly expand T cells from a patient can be used, for example, to quickly generate sufficient numbers of cells for use in tests to monitor the specificity, activity, or other attributes of a patient's T lymphocytes. Moreover, the capability of rapidly achieving cell doses of $10^9$–$10^{10}$ cells will greatly facilitate the applicability of specific adoptive immunotherapy for the treatment of human diseases.

There are several established methods already described for culturing cells for possible therapeutic use including methods to isolate and expand T cell clones. Typical cell culture methods for anchorage-dependent cells, (i.e., those cells that require attachment to a substrate for cell proliferation) are limited by the amount of surface area available in culture vessels used (i.e., multi-well plates, petri dishes, and culture flasks). For anchorage-dependent cells, the only way to increase the number of cells grown is generally to use larger vessels with increased surface area and/or use more vessels. However, hematopoietic cells such as T lymphocytes are anchorage-independent. They can survive and proliferate in response to the appropriate growth factors in a suspension culture without attachment to a substrate. Even with the ability to grow antigen-specific lymphocytes in a suspension culture, the methods reported to date have not consistently produced rapid numerical expansion of T cell clones. For example, in a study of T cells conducted by Gillis and Watson, it was found that T cells cultured at low densities, i.e., $5 \times 10^3$ to $1 \times 10^4$ cell/ml in over a seven day period and eventually reached a saturation density of $3-5 \times 10^5$ cells/ml. Gillis, S. and Watson, J. "Interleukin-2 Dependent Culture of Cytolytic T Cell Lines", *Immunological Rev.*, 54:81–109 (1981). Furthermore, Gillis and Watson also found that once cells reached this saturation concentration, the cells would invariably die. Gillis et al., id.

Another study reported three different methods for establishing murine T lymphocytes in long-term culture. Paul et al., reported that the method most widely used is to grow T lymphocytes from immunized donors for several weeks or more in the presence of antigen and antigen-presenting cells (APCs) to provide the requisite T cell receptor signal and co-stimulatory signals, and with the addition of exogenous growth factors before attempting to clone them, Paul, W. E., et al., "Long-term growth and cloning of non-transformed lymphocytes", *Nature*, 294:697–699, (1981). T cells specific for protein antigens are then cloned by limiting dilution with antigen and irradiated spleen cells as a source of APCs. A second method involved growing T cells as colonies in soft agar as soon as possible after taking the cells from an immunized donor. The T cells were stimulated in an initial suspension culture with antigen and a source of APCs, usually irradiated spleen cells. In this second approach, it was found that, after 3 days, the cells were distributed in the upper layer of a two-layer soft agar culture system. The colonies were picked from day 4 to 8 and then expanded in long-term cultures. The third approach involved selecting cells for their functional properties rather than their antigenic specificity and then growing them with a series of different irradiated feeder cells and growth factor containing supernatants. Paul, W. E. et al., "Long-term growth and cloning of non-transformed lymphocytes", *Nature*, 294:697–699, (1981). It is apparent that with each of these methods, it is not possible to expand individual T cell clones from a single cell to $10^9 - 10^{10}$ cells in a timely manner. Thus, despite the ability to clone antigen-specific T cells, and convincing evidence of the therapeutic efficacy of T cell clones in accepted animal models, the technical difficulty in culturing human T cells to large numbers has impeded the clinical evaluation and application of cellular immunotherapeutic procedures.

Yet another concern with cultured T cells is that they must remain capable of functioning in vivo in order to be useful in immunotherapeutic procedures. In particular, it has been observed that antigen-specific T cells which were grown long term in culture in high concentrations of IL-2 may develop cell cycle abnormalities and lose the ability to return to a quiescent phase when IL-2 is withdrawn. In contrast, the normal cell cycle consists of four successive phases: mitosis (or "M" phase) and three phases which make up the "interphase" stage. During the M phase, the cell undergoes nuclear division and cytokinesis. The interphase stage consists of the G1 phase in which the biosynthetic activities resume at a high rate after mitosis; the S phase in which DNA synthesis occurs and the G2 phase which continues until mitosis commences. While in the G1 phase, some cells appear to cease progressing through the division cycle; and are said to be in a "resting" or quiescent state (denoted as the "G0" state). Certain environmental factors (such as a lack of growth factors in serum or confluence of cell cultures) may cause cells to enter the quiescent state. Once the factor is restored, the cell should resume its normal progress through the cycle. However, cells grown in culture may be unable to enter the quiescent phase when the growth factor is removed, resulting in the death of these cells. This growth factor dependence is particularly relevant to cultured T cells. T lymphocytes that are exposed over a long term to high concentrations of IL-2 to promote cell growth often will die by a process called apoptosis if IL-2 is removed or if they are subsequently stimulated through the T cell receptor, i.e., if they encounter specific antigens. (see, e.g., Lenardo M. J., *Nature*, 353:858–861, 1991; Boehme S. A. and Lenardo M. J., *Eur. J. Immunol.*, 23:1552–1560, 1992). Therefore, the culture methods used to propagate LAK cells or TIL-cells, and prior methods to culture T cells which predominantly rely on high long-term concentrations of IL-2 to promote expansion in vitro, may render many of the cells susceptible to apoptosis, thus limiting or eliminating their usefulness for cellular immunotherapy.

It may also be advantageous in cellular immunotherapy studies to use gene transfer methods to insert foreign DNA into the T cells to provide a genetic marker, to facilitate evaluation of in vivo migration and survival of transferred cells, or to confer functions that may improve the safety and efficacy of transferred T cells. An established method for stable gene transfer into mammalian cells is the use of amphotropic retroviral vectors (see, e.g., Miller A D, *Current Topics in Microbiology and Immunology*, 158:1–24, 1992). The stable integration of genes into the target cell using retrovirus vectors requires that the cell be actively cycling, specifically that these cells transit M phase of the cell cycle. Prior studies have introduced a marker gene into a small proportion of polyclonal T cells driven to proliferate with high doses of IL-2, and these cells were reinfused into humans as tumor therapy and provided a means of following the in vivo survival of transferred cells. (Rosenberg et al. *New Engl. J. Med.*, 323:570–578, 1990). However, for human T cells (which cycle slowly when grown with standard techniques) the efficiency of stable gene transfer is very low, in the range of 0.1–1% of T cells. (Springett C M et al. *J. Virology*, 63:3865–69, 1989). Culture methods which more efficiently recruit the target T cells into the S and G2-M phases of the cell cycle may increase the efficiency of gene modification using retrovirus-mediated gene transfer (Roe T. et al., *EMBO J*, 2:2099–2108, 1993), thus improving the prospects for using genetically-modified T cells in cellular immunotherapy or using T cells to deliver defective genes in genetic deficiency diseases.

The rapid expansion method described by S. Riddell et al. (in PCT Publication WO 96/06929, published Mar. 7, 1996), hereinafter referred to as "high-PBMC REM" or "hp-REM" was developed to provide functional, antigen-specific T cell clones for use in clinical adoptive immunotherapy protocols. The hp-REM protocol was designed to provide maximal T cell expansion in a limited amount of time without loss of T cell function and specificity. Generally, the hp-REM protocol involves the steps of adding an initial T lymphocyte population to a culture medium in vitro; adding to the culture medium a disproportionately large number of non-dividing peripheral blood mononuclear cells ("PBMC") as feeder cells such that the resulting population of cells contains at least about 40 PBMC feeder cells (preferably at least about 200, more preferably at least about 400) for each T lymphocyte in the initial population to be expanded; and incubating the culture. In preferred embodiments of the hp-REM protocol, the T cells to be expanded are also exposed to a disproportionately large number of EBV-transformed lymphoblastoid cells ("LCL"), to an anti-CD3 monoclonal antibody (e.g., OKT3) (to activate the T cells via the T cell antigen receptor), and to the T cell growth factor interleukin-2 (IL-2).

In the hp-REM protocol, T cells are generally expanded using a vast excess of feeder cells consisting of peripheral blood mononuclear cells (PBMC) and possibly also EBV-transformed lymphoblastoid cells (EBV-LCL). T cells to be expanded typically represent less than about 0.2% of the cells in the hp-REM culture method. As described, the T cells can be activated through the T cell antigen receptor using an anti-CD3 monoclonal antibody (e.g. OKT3) and T cell proliferation can be induced using IL-2. Such hp-REM culture conditions were reported to result in a level of T cell expansion 100 to 200-fold greater than that reported by others.

However, for most uses, it would be preferable to avoid the use of large excesses of feeder cells (i.e. PBMC and EBV-LCL) in the preparation of T cells destined for clinical use. For example, PBMCs are derived from human blood and could represent a potential source of adventitious agents (e.g. human imunodeficiency virus, type 1 and 2; human T cell leukemia virus I, type 1 and 2; and hepatitis virus, such as hepatitis B, C and G), and EBV-LCL could represent a potential source of Epstein-Barr virus. In addition, the large-scale application of the hp-REM protocol would require a large supply of human peripheral blood to provide adequate numbers of feeder cells.

It would therefore be particularly advantageous to reduce the numbers of such feeder cells required or to replace them entirely. With these concerns in mind, the methods of the present invention (hereinafter referred to as "low-PBMC-REM" or "modified-REM") are designed to achieve rapid in vitro expansion of T cells without using the vast excess of PBMC and/or EBV-LCL feeder cells that are the key characteristic of the hp-REM protocol.

BRIEF SUMMARY OF THE INVENTION

This invention provides a method for rapidly producing large numbers of T cells, including human antigen-specific cytolytic and helper T cells, isolated from an initial population of T cells, without using the vast excess of PBMC and/or EBV-LCL feeder cells that are the key characteristic of the hp-REM protocol. While the methods of the present invention are applicable to the rapid expansion of T lymphocytes, generally, the rapid expansion method will be especially advantageous in situations in which an individual T cell clone must be expanded to provide a large population of T lymphocytes. Thus, the present invention provides an especially important tool in the context of human adoptive immunotherapy, as has been exemplified in studies (using hp-REM, described below) involving human bone marrow transplant recipients at the Fred Hutchinson Cancer Research Center. The present invention also provides a method to improve the efficiency of stable gene transfer into T lymphocytes, as exemplified below.

Accordingly, one object of the invention is to rapidly expand T lymphocytes to large numbers in vitro without using the vast excess of PBMC and/or EBV-LCL feeder cells that are the key characteristic of the hp-REM protocol. Such rapidly expanded T cell populations can be used, inter alia, for infusion into individuals for the purpose of conferring a specific immune response, as exemplified herein. T cells that can be expanded using the present invention include any of the various T lymphocyte populations described herein (see, e.g., the discussion above regarding CTLs, helper T cells and other T lymphocytes, and the potential uses of such cells in immunotherapeutic techniques).

Another object of the invention is to use the method to grow T cells in a manner which facilitates the stable introduction of foreign genetic material which can be used to alter the function of T cells to be used in cellular immunotherapies, as described above, or to otherwise overcome for a defective or inadequate gene in the host.

A number of preferred embodiments of the present invention are described in the following enumeration:

1. A method (referred to herein as "low-PBMC-REM" or "modified-REM") for rapidly expanding an initial T lymphocyte population in culture medium in vitro, comprising the steps of: adding an initial T lymphocyte population to a culture medium in vitro; adding to the culture medium a non-dividing mammalian cell line expressing at least one T-cell-stimulatory component, wherein said cell line is not an EBV-transformed lymphoblastoid cell line (LCL); and incubating the culture. REM cultures will generally be incubated under conditions of temperature and the like that are suitable for the growth of T lymphocytes. For the growth of human T lymphocytes, for example, the temperature will generally be at least about 25 degrees Celsius, preferably at least about 30 degrees, more preferably about 37 degrees. Descriptions of suitable media and other culture conditions are well-known in the art, and are also exemplified herein.

2. A rapid expansion method according to the preceding item, wherein said T-cell-stimulatory component is selected from the group consisting of an Fc-γ receptor, a cell adhesion-accessory molecule and a cytokine.

3. A rapid expansion method according to any of the preceding items, wherein said T-cell-stimulatory component is selected from the group consisting of an Fc-γ receptor, a cell adhesion-accessory molecule and a cytokine, and wherein said initial T lymphocyte population is expanded at least 200-fold after an incubation period of less than about two weeks.

4. A rapid expansion method according to any of the preceding items, wherein said T-cell-stimulatory component is selected from the group consisting of an Fc-γ receptor, a cell adhesion-accessory molecule and a cytokine, and wherein said initial T lymphocyte population is expanded at least 500-fold after an incubation period of less than about two weeks.

5. A rapid expansion method according to any of the preceding items, wherein said T-cell-stimulatory component is selected from the group consisting of an Fc-γ receptor, a cell adhesion-accessory molecule and a cytokine, and wherein said initial T lymphocyte population is expanded at least 1000-fold after an incubation period of less than about two weeks.

6. A rapid expansion method according to any of the preceding items, further comprising the step of adding anti-CD3 monoclonal antibody to the culture medium wherein the concentration of anti-CD3 monoclonal antibody is at least about 1.0 ng/ml. Typically, a concentration of about 10 ng/ml is employed although much lower levels can be used, as illustrated below.

7. A rapid expansion method according to any of the preceding items, further comprising the step of adding IL-2 to the culture medium, wherein the concentration of IL-2 is at least about 10 units/ml. Typically, a concentration of about 25 units/ml is used. Preferably, the incubation is continued for at least about 9 days and wherein the step of adding IL-2 to the culture medium is repeated after each 3–5 day interval. Typically, IL-2 is added on day 0, again on day 5 or 6, and again on day 8 or 9.

8. A rapid expansion method according to any of the preceding items, wherein said mammalian cell line comprises at least one cell type that is present at a frequency at least twice that found in human peripheral blood mononuclear cells (human PBMCs); preferably at least three times, at least ten times, or at least fifty times the frequency generally found in human PBMCs.

9. A rapid expansion method according to any of the preceding items, wherein said T-cell-stimulatory component is selected from the group consisting of an Fc-γ receptor and a cell adhesion-accessory molecule.

10. A rapid expansion method according to any of the preceding items, wherein said T-cell-stimulatory component is selected from the group consisting of a cell adhesion-accessory molecule and a cytokine.

11. A rapid expansion method according to any of the preceding items, wherein said T-cell-stimulatory component is selected from the group consisting of an Fc-γ receptor and a cytokine.

12. A rapid expansion method according to any of the preceding items, wherein said mammalian cell line expresses a cell adhesion-accessory molecule.

13. A rapid expansion method according to any of the preceding items, wherein said cell adhesion-accessory molecule is selected from the group consisting of Class II MHC, Class I MHC, ICAM 1, ICAM 2, ICAM 3, CD58, CD72, fibronectin, ligand to CD27, CD80, CD86 and hyaluronate.

14. A rapid expansion method according to any of the preceding items, wherein said mammalian cell line expresses a cytokine. Preferably the cytokine is an interleukin.

15. A rapid expansion method according to any of the preceding items, wherein said T-cell-stimulatory component is a molecule that binds to CD21.

16. A rapid expansion method according to any of the preceding items, wherein said cytokine is selected from the group consisting of IL-1, IL-2, IL-4, IL-6, IL-7, IL-12 and IL-15.

17. A rapid expansion method according to any of the preceding items, further comprising the step of adding a soluble T-cell-stimulatory factor to the culture medium.

18. A rapid expansion method according to any of the preceding items, wherein said soluble T-cell-stimulatory factor is selected from the group consisting of a cytokine, an antibody specific for a T cell surface component, and an antibody specific for a component capable of binding to a T cell surface component.

19. A rapid expansion method according to any of the preceding items, wherein said soluble T-cell-stimulatory factor is a cytokine selected from the group consisting of IL-1, IL-2, IL-4, IL-6, IL-7, IL- 12 and IL-15.

20. A rapid expansion method according to any of the preceding items, wherein said soluble T-cell-stimulatory factor is an antibody specific for a T cell surface component, and wherein said T cell surface component is selected from the group consisting of CD4, CD8, CD11a, CD2, CD5, CD49d, CD27, CD28 and CD44.

21. A rapid expansion method according to any of the preceding items, wherein said soluble T-cell-stimulatory factor is an antibody specific for a component capable of binding to a T cell surface component, and wherein said T cell surface component is selected from the group consisting of CD4, CD8, CD11a, CD2, CD5, CD49d, CD27, CD28 and CD44.

22. A rapid expansion method according to any of the preceding items, wherein said soluble T-cell-stimulatory factor is a molecule that binds to CD21.

23. A rapid expansion method according to any of the preceding items, wherein said molecule that binds to CD21 is an anti-CD21 antibody.

24. A rapid expansion method according to any of the preceding items, further comprising the step of adding to the culture a multiplicity of peripheral blood mononuclear cells (PBMCs). Preferably, PBMC are irradiated with gamma rays in the range of about 3000 to 3600 rads, more preferably at about 3300 rads.

25. A rapid expansion method according to any of the preceding items, wherein the ratio of PBMCs to initial T cells to be expanded is less than about 40:1.

26. A rapid expansion method according to any of the preceding items, wherein the ratio of PBMCs to initial T cells to be expanded is less than about 10:1.

27. A rapid expansion method according to any of the preceding items, wherein the ratio of PBMCs to initial T cells to be expanded is less than about 3:1.

28. A rapid expansion method according to any of the preceding items, further comprising the step of adding to the culture a multiplicity of EBV-transformed lymphoblastoid cells (LCLs). Preferably, PBMC are irradiated with gamma rays in the range of about 6000 to 10,000 rads, more preferably at about 8000 rads.

29. A rapid expansion method according to any of the preceding items, wherein the ratio of LCLs to initial T cells to be expanded is less than about 10:1.

30. A rapid expansion method according to any of the preceding items, wherein the initial T lymphocyte population comprises at least one human CD8+ antigen-specific cytotoxic T lymphocyte (CTL). In preferred embodiments of the present invention, the CTL is specific for an antigen present on a human tumor or encoded by a pathogen such as a virus or bacterium.

31. A rapid expansion method according to any of the preceding items, wherein the initial T lymphocyte population comprises at least one human CD4+ antigen-specific helper T lymphocyte.

32. A method of genetically transducing a human T cell, comprising the steps of: adding an initial T lymphocyte population to a culture medium in vitro; adding to the culture medium a non-EBV-transformed mammalian cell line expressing a T-cell-stimulatory component; and incubating the culture; and adding a vector to the culture medium. A vector refers to a unit of DNA or RNA in a form which is capable of being introduced into a target cell. Transduction is used generally to refer to the introduction of such exogenous DNA or RNA into a target cell and includes the introduction of heterologous DNA or RNA sequences into target cells by, e.g., viral infection and electroporation. A currently preferred method of transducing T lymphocytes is to use retroviral vectors, as exemplified herein.

33. A genetic transduction method according to item 32, wherein the vector is a retroviral vector containing a selectable marker providing resistance to an inhibitory compound that inhibits T lymphocytes, and wherein the method further comprises the steps of: continuing incubation of the culture for at least one day after addition of the retroviral vector; and adding said inhibitory compound to the culture medium after said continued incubation step. Preferably, the retroviral vector contains both a positive and a negative selectable marker. Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene.

34. A genetic transduction method according to any of items 32–33, further comprising adding a multiplicity of human PBMCs.

35. A rapid expansion method according to any of items 32–34, wherein the ratio of PBMCs to initial T cells is less than about 40:1.

36. A genetic transduction method according to any of items 32–35, further comprising adding non-dividing EBV-transformed lymphoblastoid cells (LCL).

37. A rapid expansion method according to any of items 32–36, wherein the ratio of LCL to initial T cells is less than about 10:1.

38. A method of generating a REM cell line capable of promoting rapid expansion of an initial T lymphocyte population in vitro, comprising the steps of: depleting one or more cell types from a human PBMC population to produce a cell-type-depleted PBMC population, using said cell-type-depleted PBMC population in place of non-depleted PBMCs in an hp-REM protocol to determine the contribution of the depleted cell type to the activity provided by the non-depleted PBMCs, identifying a T cell stimulatory activity provided by said depleted cell type, and transforming a mammalian cell line with a gene allowing expression of said T cell stimulatory activity.

39. A method of generating a REM cell line according to item 38, wherein said T-cell-stimulatory component is selected from the group consisting of an Fc-γ receptor, a cell adhesion-accessory molecule and a cytokine.

40. A REM cell line capable of stimulating rapid expansion of an initial T lymphocyte population in vitro, comprising a mammalian cell line generated according to a method according to the preceding item 38 or item 39.

41. A REM cell line according to item 40, wherein said cell line expresses a cell adhesion-accessory molecule.

42. A REM cell line according to any of items 40–41, wherein said cell adhesion-accessory molecule is selected from the group consisting of Class II MHC, Class I MHC, ICAM 1, ICAM 2, ICAM 3, CD58, CD72, fibronectin, ligand to CD27, CD80, CD86 and hyaluronate.

43. A REM cell line according to any of items 40–42, wherein said cell line expresses an Fc-γ receptor.

44. A REM cell line according to any of items 40–43, wherein said cell line expresses at least one T cell stimulatory cytokine.

45. A REM cell line according to any of items 40–44, wherein said T cell stimulatory cytokine is selected from the group consisting of IL-1, IL-2, IL-6, IL-7, IL-12 and IL-15.

46. A REM cell line according to any of items 40–44, wherein said cell line expresses a molecule that binds CD21. As used herein, a molecule that binds CD21 can be a natural or synthetic molecule known or determined to bind to the CD21 cell surface determinant. Molecules known to bind to CD21 include anti-CD21 antibodies, as well as molecules such as C3d, C3dg, iC3b and EBV gp350/220, and derivatives thereof.

47. A culture medium capable of rapidly expanding an initial T lymphocyte population in vitro comprising a REM cell line according to any of items 40–46.

48. A culture medium according to item 47, further comprising an exogenous cytokine.

49. A culture medium according to any of items 47–48, further comprising a multiplicity of exogenous cytokines, wherein said multiplicity comprises at least one interleukin.

50. A culture medium according to any of items 47–49, wherein said interleukin is selected from the group consisting of IL-1, IL-2, IL-6, IL-7, IL-12 and IL-15.

51. A culture medium according to any of items 47–50, further comprising a molecule that binds to CD21. As used herein, a molecule that binds CD21 can be a natural or synthetic molecule known or determined to bind to the CD21 cell surface determinant. Molecules known to bind to CD21 include anti-CD21 antibodies, as well as molecules such as C3d, C3dg, iC3b and EBV gp350/220, and derivatives thereof that bind to CD21.

52. A culture medium according to item 51, wherein said molecule that binds to CD21 is an anti-CD21 antibody.

53. A culture medium according to any of items 49–52, further comprising an anti-CD3 monoclonal antibody.

DETAILED DESCRIPTION OF PREFERRED EMBODIMENTS AND APPLICATIONS OF THE INVENTION

The invention described herein provides methods for rapidly expanding populations of T lymphocytes, including human cytotoxic T lymphocytes and helper T lymphocytes, which can be particularly useful in cellular immunotherapy of human diseases, without using the vast excess of PBMC and/or EBV-LCL feeder cells that are the key characteristic of the hp-REM protocol.

The T cells will be referred to as "target T cells". In general, target T cells are added in small numbers to a culture vessel containing standard growth medium that has been supplemented with components that stimulate rapid expansion in vitro (REM) as described herein. Preferably, human recombinant IL-2 or another suitable IL-2 preparation is added in low concentrations at 3–5 day intervals (typically on "day 0"(i.e. at culture initiation) or "day 1"(the day following inititiation), again on day 5 or 6, and again on day 8 or 9). REM protocols result in a rapid expansion of T cells, typically in the range of a 500- to 3000-fold expansion within 8 to 14 days. Such methods can thus achieve expansion rates that are approximately 100- to 1000-fold more efficient for each stimulation cycle than previously-described methods of culturing human T cells.

Furthermore, REM protocols are applicable to the rapid expansion of any T cell sub-population including helper T cells and cytolytic T cells; and to T cell clones of many different antigenic specificities (e.g., to cytolytic or helper T cells specific for CMV, HIV, or other viral, bacterial, or tumor-derived antigens). In addition, REM protocols can be used for both small scale growth (e.g. to rapidly expand T cells from $10^4$ to $10^7$ cells); or for large-scale expansions (e.g. to rapidly expand T cells from $10^6$ to greater than $10^{10}$ cells); depending on the size of culture vessel chosen.

REM protocols thus make it possible to efficiently expand T cell clones for use in adoptive immunotherapies by dramatically shortening the time required to grow the numbers of cells required to restore, enhance, or modulate human immunity. In the study by Riddell et al. (*Science*, 257:238–240, 1992), once T cell clones were isolated it was necessary to culture the clones for twelve weeks and to pool multiple clones to achieve the highest administered cell dose of $1 \times 10^9$ CD8+ CMV-specific T cells/m² body surface area. Using REM protocols, the expansion of individual T cell clones to greater than $10^9$ cells can be accomplished in less than three weeks.

With respect to the rapid expansion methods (i.e. "REM" technology), the following abbreviations are used to distinguish the various REM protocols referred to herein. The basic Riddell protocol (as described above and in the cited Riddell patent application), which uses a disproportionately large number of PBMC feeder cells (and preferably also EBV-LCL feeder cells) is referred to as "high-PBMC REM" or simply "hp-REM". Conversely, the methods of the present invention, which do not employ such large excesses of PBMC feeder cells (and preferably no EBV-LCL feeder cells) are referred to as "low-PBMC REM" or "modified-REM". Such methods are described in detail below.

The practice of the present invention will employ, unless otherwise indicated, conventional techniques of molecular biology, microbiology, cell biology, recombinant DNA, and immunology, which are within the skill of the art. Such techniques are explained fully in the literature. See e.g., Sambrook, Fritsch, and Maniatis, *Molecular Cloning: A Laboratory Manual*, Second Edition (1989); *Animal Cell Culture* (R. I. Freshney, Ed., 1987); *Gene Transfer Vectors for Mammalian Cells* (J. M. Miller and M. P. Calos eds. 1987); *Handbook of Experimental Immunology*, (D. M. Weir and C. C. Blackwell, Eds.); Current Protocols in Molecular Biology (F. M. Ausubel, R. Brent, R. E. Kingston, D. D. Moore, J. G. Siedman, J. A. Smith, and K. Struhl, eds., 1987); Current Protocols in Immunology (J. E. Coligan, A. M. Kruisbeek, D. H. Margulies, E. M. Shevach and W. Strober, eds., 1991); *Oligonucleotide Synthesis* (M. J. Gait Ed., 1984); and the series *Methods in Enzymology* (Academic Press, Inc.).

All patents, patent applications, and publications mentioned herein, both supra and infra, are hereby incorporated herein by reference.

As an aid in understanding this invention, the following is a list of some abbreviations commonly used herein:

CTL cytotoxic T lymphocyte(s)
APC antigen-presenting cell(s)
CMV cytomegalovirus
HIV human immunodeficiency virus
EBV Epstein Barr virus
hIL-2 human interleukin-2
MHC major histocompatibility complex
PBMC peripheral blood mononuclear cell(s)
EBV-LCL EBV-transformed lymphoblastoid cell line (sometimes abbreviated as simply "LCL")
PBS phosphate buffered solution
REM rapid expansion method
hp-REM high-PBMC REM
lp-REM low-PBMC or "modified" REM A "cytokine," as used herein, refers to any of a variety of intercellular signaling molecules (the best known of which are involved in the regulation of mammalian somatic cells). A number of families of cytokines, both growth promoting and growth inhibitory in their effects, have been characterized including, for example: interleukins (such as IL-1α, IL-1β, IL-2, IL-3, IL-4, IL-5, IL-6, IL-7, IL-8, IL-9 (P40), IL-10, IL-11, IL-12, IL-13, IL-14, and IL-15); CSF-type cytokines such as GM-CSF, G-CSF, M-CSF, LIF, EPO, TPO ("thrombopoietin"), TNF-α, and TNF-β); interferons (such as IFN-α, IFN-β, IFN-γ); cytokines of the TGF-β family (such as TGF-β1, TGF-β2, TGF-β3, inhibin A, inhibin B, activin A, activin B); growth factors (such as EGF, VEGF, SCF ("stem cell factor" or "steel factor"), TGF-α, aFGF, bFGF, KGF, PDGF-A, PDGF-B, PD-ECGF, INS, IGF-I, IGF-II, NGF-β); α-type intercrine cytokines (such as IL-8, GRO/MGSA, PF-4, PBP/CTAP/βTG, IP-10, MIP-2, KC, 9E3); and β-type intercrine cytokines (such as MCAF, ACT-2/PAT 744/G26, LD-78/PAT 464, RANTES, G26, I309, JE, TCA3, MIP-1α, B, CRG-2); and chemotactic factors (such as NAP-1, MCP-1, MIP-1α, MIP-1β, MIP-2, SISβ, SISδ, SISε, PF-4, PBP, γIP-10, MGSA). A number of other cytokines are also known to those of skill in the art. The sources, characteristics, targets and effector activities of these cytokines have been described and, for many of the cytokines, the DNA sequences encoding the molecules are also known; see, e.g., R. Callard & A. Gearing, *The Cytokine Facts Book* (Academic Press, 1994), and the particular publications reviewed and/or cited therein, which are hereby incorporated by reference in their entirety. As referenced in catalogs such as *The Cytokine Facts Book*, many of the DNA and/or protein sequences encoding such cytokines are also generally available from sequence databases such as GEN-BANK (DNA); and/or SWISSPROT (protein). Typically, cloned DNA encoding such cytokines will already be available as plasmids, although it is also possible to synthesize polynucleotides encoding the cytokines based upon the published sequence information. Polynucleotides encoding the cytokines can also be obtained using polymerase chain reaction (PCR) methodology, as described in the art. *See*, e.g., Mullis & Faloona, *Met. Enzymology*, 155: 355 (1987). The detection, purification, and characterization of cytokines, including assays for identifying new cytokines effective upon a given cell type, have also been described in a number of publications as well as the references referred to herein. *See*, e.g., *Lymphokines and Interferons*, 1987; and DeMaeyer, E., et al., "Interferons and Other Regulatory Cytokines," (John Wiley & Sons 1988).

A mammalian "cell line", as used herein, refers to a population of mammalian cells (preferably human cells) that have undergone repeated propagation in vitro; as distinguished from "primary cells" taken from an individual such as a human. Generally, a mammalian cell line will have been propagated in vitro for at least about 10 generations, more typically at least about 40 generations, most typically at least about 100 generations. Most preferably, the mammalian cell line can be propagated and maintained long term (i.e., at least several months in vitro, preferably at least a year). Such cell lines would include, but are not limited to, "clonal" lines (in which all of cells of the population are derived from a single ancestral cell). Conversely, a mixed peripheral blood population such as PBMCs would not constitute a mammalian cell line. A mammalian cell line for use in the present invention may, however, contain a cell type found in peripheral blood but in that case the cell type will generally be present at a frequency much higher than is normally found in human peripheral blood mononuclear cells (at least twice the frequency generally found in human peripheral blood mononuclear cells; preferably at least five times, at least ten times, at least twenty times or at least fifty times the frequency generally found in human peripheral blood mononuclear cells). A particular "cell type" might be, for example, one of the cell types typically found in peripheral blood (such as B lymphocytes, monocytes, cytotoxic T lymphocytes, helper T lymphocytes, granulocytes, eosinophils or NK cells); or of a cell type not normally found in peripheral blood (such as fibroblasts, endothelial cells, etc.); or a more specific subpopulation of such a cell type (e.g. a subpopulation that is relatively homogeneous with respect to antigen-specificity or expression of a particular receptor). Thus, a cell line might be relatively homogeneous with respect to attributes such as antigen-specificity or cell surface receptors/ligands, as discussed in more detail below. By way of illustration, a receptor-specific monocyte line refers to a population of cells in vitro in which the majority of cells are monocytes possessing a particular cell surface receptor (which cell line might have been obtained for example by transforming a population of monocytes with genes expressing the particular receptor). Again, by way of illustration, an antigen-specific CTL cell line refers to a population of cells in vitro in which the majority of cells are cytotoxic T lymphocytes specific for a particular antigen such as a viral, bacterial or tumor antigen (which cell line might have been obtained for example by exposing a population of T cells to repeated stimulation with a particular antigen and subsequently enriching for antigen-specific CTLs).

Preferably, such a cell line for use with the present invention will be rendered non-dividing prior to use in the modified-REM culture (e.g., by irradiation). However, one can alternatively (or in addition) employ a cell line that is dividing (preferably at a rate similar to or slower than the expanding T cells) but which can be subsequently eliminated by virtue of its having a negative selectable marker (e.g., a suicide gene that can be used to inhibit or kill cells carrying the gene, or a cell surface marker that can be used to isolate and/or eliminate cells carrying the marker). In the latter case, the cell line can be allowed to expand to some degree in the REM culture before being negatively selected.

Preferably, mammalian cell lines to be used with the present invention are relatively homogeneous lines (i.e. at least 50% of the cells are of a particular cell type, more preferably at least 70%, at least 90%, at least 95% or at least 99% of the cells are of a particular cell type). It should be noted, however, that T cells to be expanded by exposure to such a cell line might also be exposed to additional cell lines (at the same time or in sequence). Thus, by way of illustration, a modified-REM culture (containing a T lymphocyte population to be expanded) might be exposed to one mammalian cell line or to several such lines. For modified-REM, T cells to be expanded will be exposed to at least one such mammalian cell line and/or to a non-cellular mixture of factors (including, e.g., cytokines, antibodies, soluble ligands, etc.), as discussed herein.

The T cells to be propagated in culture (i.e., the "target" T-cells) can be obtained from the subject to be treated. Alternatively, T cells can be obtained from a source other than the subject to be treated, in which case the recipient and transferred cells are preferably immunologically compatible (or the receipient is otherwise made immuno-tolerant of the transferred cells). Typically, the target T cells are derived from tissue, bone marrow, fetal tissue, or peripheral blood. Preferably, the cells are derived from peripheral blood. If the T cells are derived from tissues, single cell suspensions can be prepared using a suitable medium or diluent.

Mononuclear cells containing the T lymphocytes can be isolated from the heterogenous population according to any of the methods well known in the art. As illustrative examples, Ficoll-Hypaque gradient centrifugation, fluorescence-activated cell sorting (FACs), panning on monoclonal antibody coated plates, and/or magnetic separation techniques can be used (separately or in combination) to obtain purified populations of cells for expansion according to the present invention. Antigen-specific T cells can be isolated by standard culture techniques known in the art involving initial activation of antigen-specific T cell precursors by stimulation with antigen-presenting cells and, for a clonal population, by limiting dilution cultures using techniques known in the art, such as those described in Riddell and Greenberg (*J. Immunol. Meth.*, 128:189–201, 1990); and Riddell et al. (*J.Immunol.*, 146:2795–2804, 1991). See also, the Examples below. T cell clones isolated in microwells in limiting dilution cultures typically have expanded from a single cell to $2 \times 10^4$ to $5 \times 10^5$ cells after 14 days.

For expansion, T cells can be placed in appropriate culture media in plastic culture vessels with T cell stimulatory components as described herein. The initial phase of rapid expansion is generally carried out in a culture vessel, the size of which depends upon the number of target cells, and which may typically be a 25 cm² flask. The size of the culture vessel used for subsequent cycles of T cell expansion depends on the starting number of T cells and the number of cells needed. Typical starting cell numbers for different sized culture vessels are as follows: $5 \times 10^4$ to $2 \times 10^5$—approximately 25cm² flask; $2 \times 10^5$ to $5 \times 10^5$—approximately 75² cm flask; $5 \times 10^5$ to $1 \times 10^6$—approximately 225-cm² flask; and $1 \times 10^6$ to $2 \times 10^6$—roller bottle. The approximate initial volume of media used with each flask is: 25 cm²—20–30 ml; 75 cm²—60–90 ml; 225 cm²—100–200 ml; roller bottle—500 ml.

For even larger-scale expansions, a variety of culture means can be used, including for example, spinner flasks, cell culture bags, and bioreactors (such as hollow-fiber bioreactors).

As used herein, "feeder cells" are accessory cells that provide co-stimulating functions in conjunction with T cell receptor activation (which can be achieved by ligation of the T cell receptor complex with anti-CD3 monoclonal antibody). PBMC feeder cells for use in REM can be obtained by techniques known in the art, for example by leukaphoresis, which is a standard medical procedure with minimal risks (see, e.g., Weaver et al., *Blood* 82:1981–1984, 1993); and these feeder cells can be stored by cryopreservation in liquid nitrogen until use. LCL can be generated from peripheral blood B cells by transformation with EBV, for example the B95-8 strain of EBV, using standard methods (see, e.g., Crossland et al., *J. Immunol.* 146:4414–20, 1991), or by spontaneous outgrowth in the presence of cyclosporin A. Such LCL cells will grow rapidly and indefinitely in culture.

Prior to adding any feeder cells to the culture vessel (whether PBMCs or cells derived from a cell line as described herein), such feeder cells are preferably prevented from undergoing mitosis. Techniques for preventing mitosis are well known in the art and include, for example irradiation. For example, any PBMCs can be irradiated with gamma rays in the range of about 3000 to 4000 rads (preferably PBMCs are irradiated at about 3600 rads); any LCL can be irradiated with gamma rays in the range of about 6000–12,000 rads (preferably LCL are irradiated at about 10,000 rads); and any cells derived from other cell lines can also be irradiated with gamma rays in the range of about 6000–12,000 rads. As discussed above, negatively selectable feeder cells can also be used.

Since the antigen specificity of the T cell clone is generally defined prior to expanding the cell in the culture system, either autologous or allogeneic feeder cells can be used to support T cell growth. The ability to use allogeneic feeder cells is important in situations in which the patient is infected with a virus that is present in PBMC, e.g., HIV, that could therefore contaminate the T cell cultures. In such circumstances, the use of allogeneic feeder cells derived from an individual that is screened and deemed to be a suitable blood donor by American Red Cross criteria can be used in the culture method.

The T cell receptor activation signal (normally provided by antigen and antigen-presenting cells) can be achieved by the addition anti-CD3 monoclonal antibodies to the culture system. The anti-CD3 monoclonal antibody most commonly used is "OKT3", which is commercially available from Ortho Pharmaceuticals in a formulation suitable for clinical use. The use of anti-CD3 ("αCD3") mAb rather than antigen as a means of ligating the T cell receptor bypasses the need to have a source of antigen-presenting cells, which for virus-specific T cells would require maintaining large numbers of suitable autologous cells and infecting these cells in vitro with high titer virus. A concentration of anti-CD3 monoclonal antibody of at least about 0.5 ng/ml, preferably at least about 1 ng/ml, more preferably at least about 2 ng/ml, promoted the rapid expansion of the T cells such that a 500- to 3000-fold expansion can be achieved within about 10 to 13 days of growth. Typically, a concentration of about 10 ng/ml anti-CD3 monoclonal antibody was used.

Of course, as an alternative to anti-CD3 monoclonal antibody, the T cell receptors can be activated and the cells stimulated by the addition of antigen-presenting cells, as described in Riddell et al., *J. Immunol.* 146:2795–2904, 1991. Suitable antigen-presenting cells include, for example, viral infected cells, tumor cells, and cells pulsed with the relevant peptide antigen.

The culture media for use in the methods of the invention can be any of the commercially available media, preferably one containing: RPMI, 25 mM HEPES, 25 $\mu$M 2-mercaptoethanol, 4 mM L-glutamine, and 11% human AB serum. Fetal calf serum can be substituted for human AB serum. Preferably, after addition of any feeder cells, anti-CD3 monoclonal antibody, and culture media are added to the target T cells, and the mixture is allowed to incubate at 37° C. in a 5% $CO_2$ humidified atmosphere under standard cell culture conditions which are well known in the art. Typically, such conditions may include venting, and addition of $CO_2$ if necessary (e.g., 5% $CO_2$, in a humidified incubator).

Preferably, the medium is also supplemented with interleukin-2 (IL-2). Typically recombinant human IL-2 is used, although a functional equivalent thereof may also be used. Preferably, IL-2 is added on day 1, and is re-added at 3–5 day intervals. Thus, IL-2 was generally added on day 1, on day 5 or 6, and again on day 8 or 9. Expansion can be improved by using an IL-2 concentration of at least about 5 U/ml, more preferably at least about 10 U/ml. Generally, a concentration of about 25 U/ml can be used.

As described in Riddell et al., supra, antigen-specific T cells expanded using REM retained their antigen-specific functionality. For example, four different HIV-specific CD8+ cytotoxic T cell clones retained the ability to kill virus-infected cells expressing the relevant antigen (i.e. HIV), and did not acquire non-specific cytolytic activities against irrelevant virus-infected or transformed target cells. Similarly, four different CMV-specific CD8+ cytotoxic T cell clones retained the ability to kill CMV-infected cells, and did not acquire non-specific cytolytic activities against irrelevant virus-infected or transformed target cells. These characteristics were also applicable to CD4+ helper T cells. Thus, antigen-specific CD4+ T cells propagated using REM retained the ability to proliferate in response to the appropriate viral antigens and appropriate antigen-presenting cells (APC). Furthermore, antigen-specific T cells cultured under REM were also capable of entering a quiescent, non-dividing phase of the cell cycle; and were capable of remaining viable for at least 4 weeks in vitro. Thus, aliquots of T cells can be removed from the cultures at the end of a stimulation cycle (generally day 12–14), and placed in a culture vessel with a roughly equal number of irradiated PBMC (without anti-CD3 mAb, antigen or IL-2).

The addition of irradiated PBMC as feeder cells during storage of expanded populations improved the ability of the T cells to enter a resting phase and to remain viable. Preferably, the ratio of PBMC feeder cells to resting T cells during storage is at least about 2:1. Without the addition of PBMC feeder cells, viability of the T cells generally drops significantly (typically to levels of about 10% or less).

As described in Riddell et al., supra, T cells expanded by REM assumed a small round morphology and 60–95% remained viable by trypan blue dye exclusion even after 28 days in culture. T cells propagated by hp-REM also entered a resting phase upon IL-2 withdrawal; and they did not undergo programmed cell death (i.e. apoptosis) upon restimulation via the antigen-specific T cell receptor. Upon restimulation (e.g. with anti-CD3 mAb or antigen), the T cells required responsiveness to IL-2, and can enter the S and G2 phases of the cell cycle and increased in cell number. Such characteristics are believed to be important for in vivo survival of the cells and for the efficacy of cellular immunotherapy. In contrast, certain previously-described methods for the propagation of T cells have been reported to cause apoptotic cell death in a proportion of cells after cytokine withdrawal or T cell receptor restimulation (see, e.g., Boehme S A and Lenardo M J, *Eur. J. Immunol.*, 23:1552–1560, 1992).

There are a number of different circumstances in which the introduction of functional genes into T cells to be used in immunotherapy may be desirable. For example, the introduced gene or genes may improve the efficacy of therapy by promoting the viability and/or function of transferred T cells; or they may provide a genetic marker to permit selection and/or evaluation of in vivo survival or migration; or they may incorporate functions that improve the safety of immunotherapy, for example, by making the cell susceptible to negative selection in vivo as described by Lupton S. D. et al., *Mol. and Cell Biol.*, 11:6 (1991); and Riddell et al., Human Gene Therapy 3:319–338 (1992); see also the publications of WO/92 08796 and WO/94 28143 by Lupton et al., describing the use of bifunctional selectable fusion genes derived from fusing a dominant positive selectable marker with a negative selectable marker.

Various infection techniques have been developed which utilize recombinant infectious virus particles for gene delivery. This represents a currently preferred approach to the transduction of T lymphocytes of the present invention. The viral vectors which have been used in this way include virus vectors derived from simian virus 40 (SV40) (see, e.g., Karlsson et al., Proc. Natl. Acad. Sci. USA 84 82:158, 1985); adenoviruses (see, e.g., Karlsson et al., EMBO J. 5:2377, 1986); adeno-associated virus (AAV) (see, e.g., B. J. Carter, Current Opinion in Biotechnology 1992, 3:533–539); and retroviruses (see, e.g., Coffin, 1985, pp. 17–71 in Weiss et al. (eds.), RNA Tumor Viruses, 2nd ed., Vol. 2, Cold Spring Harbor Laboratory, New York). Thus, gene transfer and expression methods are numerous but essentially function to introduce and express genetic material in mammalian cells. A number of the above techniques have been used to transduce hematopoietic or lymphoid cells, including calcium phosphate transfection (see, e.g., Berman et al., supra, 1984); protoplast fusion (see, e.g., Deans et al., supra, 1984); electroporation (see, e.g., Cann et al., Oncogene 3:123, 1988); and infection with recombinant adenovirus (see, e.g., Karlsson et al., supra; Reuther et al., Mol. Cell. Biol. 6:123, 1986); adeno-associated virus (see, e.g., LaFace et al., supra); and retrovirus vectors (see e.g., Overell et al., Oncogene 4:1425, 1989). Primary T lymphocytes have been successfully transduced by electroporation (see, e.g., Cann et al., supra, 1988) and by retroviral infection (see e.g., Nishihara et al., Cancer Res. 48:4730, 1988; Kasid et al., supra, 1990; and Riddell, S. et al., Human Gene Therapy 3:319–338, 1992).

Retroviral vectors provide a highly efficient method for gene transfer into eukaryotic cells. Moreover, retroviral integration takes place in a controlled fashion and results in the stable integration of one or a few copies of the new genetic information per cell.

Retroviruses are a class of viruses which replicate using a virus-encoded, RNA-directed DNA polymerase, or reverse transcriptase, to replicate a viral RNA genome to provide a double-stranded DNA intermediate which is incorporated into chromosomal DNA of an avian or mammalian host cell. Most retroviral vectors are derived from murine retroviruses. Retroviruses adaptable for use in accordance with the present invention can, however, be derived from any avian or mammalian cell source. These retroviruses are preferably amphotropic, meaning that they are capable of infecting host cells of several species, including humans. A characteristic feature of retroviral genomes (and retroviral vectors used as described herein) is the retroviral long terminal repeat, or LTR, which is an untranslated region of about 600 base pairs found in slightly variant forms at the 5' and 3' ends of the retroviral genome. When incorporated into DNA as a provirus, the retroviral LTR includes a short direct repeat sequence at each end and signals for initiation of transcription by RNA polymerase II and 3' cleavage and polyadenylation of RNA transcripts. The LTR contains all other cis-acting sequences necessary for viral replication.

A "provirus" refers to the DNA reverse transcript of a retrovirus which is stably integrated into chromosomal DNA in a suitable host cell, or a cloned copy thereof, or a cloned copy of unintegrated intermediate forms of retroviral DNA. Forward transcription of the provirus and assembly into infectious virus occurs in the presence of an appropriate helper virus or in a cell line containing appropriate sequences enabling encapsidation without coincident production of a contaminating helper virus. Mann et al. (Cell 33:153, 1983) describe the development of cell lines (e.g., Ψ2) which can be used to produce helper-free stocks of recombinant retrovirus. These cells lines contain integrated retroviral genomes which lack sequences required in cis for encapsidation, but which provide all necessary gene product in trans to produce intact virions. The RNA transcribed from the integrated mutant provirus cannot itself be packaged, but these cells can encapsidate RNA transcribed from a recombinant retrovirus introduced into the same cell. The resulting virus particles are infectious, but replication-defective, rendering them useful vectors which are unable to produce infectious virus following introduction into a cell lacking the complementary genetic information enabling encapsidation. Encapsidation in a cell line harboring trans-acting elements encoding an ecotropic viral envelope (e.g., Ψ2) provides ecotropic (limited host range) progeny virus. Alternatively, assembly in a cell line containing amphotropic packaging genes (e.g., PA317, ATCC CRL 9078; Miller and Buttimore, Mol. Cell. Biol. 6:2895, 1986) provides amphitropic (broad host range) progeny virus. Such packing cell lines provide the necessary retroviral gag, pol and env proteins in trans. This strategy results in the production of retroviral particles which are highly infectious for mammalian cells, while being incapable of further replication after they have integrated into the genome of the target cell. The product of the env gene is responsible for the binding of the retrovirus to viral receptors on the surface of the target cell and therefore determines the host range of the retrovirus. The PA 317 cells produce retroviral particles with an amphotropic envelope protein, which can transduce cells of human and other species origin. Other packaging cell lines produce particles with ecotropic envelope proteins, which are able to transduce only mouse and rat cells.

Numerous retroviral vector constructs have been used successfully to express many foreign genes (see, e.g., Coffin, in Weiss et al. (eds.), RNA Tumor Viruses, 2nd ed., vol. 2 (Cold Spring Harbor Laboratory, New York, 1985, pp. 17–71). Retroviral vectors with inserted sequences are generally functional, and few sequences that are consistently inhibitory for retroviral infection have been identified. Functional polyadenylation motifs inhibit retroviral replication by blocking retroviral RNA synthesis, and there is an upper size limit of approximately 11 kb of sequence which can be packaged into retroviral particles (Coffin, supra, 1985); however, the presence of multiple internal promoters, initially thought to be problematic (Coffin, supra, 1985), was found to be well tolerated in several retroviral constructs (Overell et al., Mol. Cell. Biol. 8:1803, 1983).

Retroviral vectors have been used as genetic tags by several groups to follow the development of murine hematopoietic stem cells which have been transduced in vitro with retrovirus vectors and transplanted into recipient mice (Williams et al., Nature 310:476, 1984; Dick et al., Cell 42:71, 1985; Keller et al., Nature 318:149, 1985). These studies have demonstrated that the infected hematopoietic cells reconstitute the hematopoietic and lymphoid tissue of the recipient animals and that the cells display a normal developmental potential in vivo. The marked cells can be visualized using any of a number of molecular biological techniques which can demonstrate the presence of the retroviral vector sequences, most notably Southern analysis and PCR (polymerase chain reaction). The ability to mark cells genetically using retroviral vectors is also useful in clinical settings in which the technique can be used to track grafts of autologous cells. This approach has already been used to track TILs (tumor-infiltrating lymphocytes) in patients given TIL therapy for terminal cancer treatment by Rosenberg et al. (N. Engl. J. Med. 323:570, 1990). The transduction of these cells with the marker gene was not associated with in vitro cellular dysfunction (Kasid et al., Proc. Natl. Acad. Sci. USA 87:473, 1990).

Many gene products have been expressed in retroviral vectors. This can either be achieved by placing the sequences to be expressed under the transcriptional control of the promoter incorporated in the retroviral LTR, or by placing them under the control of a heterologous promoter inserted between the LTRs. The latter strategy provides a way of coexpressing a dominant selectable marker gene in the vector, thus allowing selection of cells which are expressing specific vector sequences.

It is contemplated that overexpression of a stimulatory factor (for example, a lymphokine or a cytokine) may be toxic to the treated individual. Therefore, it is within the scope of the invention to include gene segments that cause the T cells of the invention to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene (Wigler et al., Cell 11:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In addition, it is useful to include in the T cells a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the aminoglycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

Preferably, the positive selectable marker and the negative selectable element are linked such that loss of the negative selectable element necessarily also is accompanied by loss of the positive selectable marker. Even more preferably, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See Lupton S. D., et al., Mol. and Cell. Biology 11:3374–3378, 1991. In addition, in preferred embodiments, the polynucleotides of the invention encoding the chimeric receptors are in retroviral vectors containing the fused gene, particularly those that confer hygromycin B resistance for positive selection in vitro, and ganciclovir sensitivity for negative selection in vivo, for example the HyTK retroviral vector described in Lupton, S. D. et al. (1991), supra. See also the publications of PCT/US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene.

A variety of methods can be employed for transducing T lymphocytes, as is well known in the art. Typically, one can carry out retroviral transductions as follows: on day 1 after stimulation using REM as described herein, one can provide the cells with 20–30 units/ml IL-2; on day 1, 2, or 3, one half of the medium can be replaced with retroviral supernatant prepared according to standard methods and the cultures supplemented with 5 $\mu$g/ml polybrene and 20–30 units/ml IL-2; on day 4, the cells are washed and placed in fresh culture medium supplemented with 20–30 units/ml IL-2; on day 5, the exposure to retrovirus can be repeated; on day 6, the cells can be placed in selective medium (containing, e.g., an antibiotic corresponding to an antibiotic resistance gene provided in the retroviral vector) supplemented with 30 units/ml IL-2; on day 13, viable cells can be separated from dead cells using Ficoll Hypaque density gradient separation and then the viable cells can be subcloned using REM.

Using an antigen-specific CTLs (55E1, an EBV-specific CD8+ clonal line) and a retroviral vector (LAPSN, Clowes et al., 1994, J. Clin. Invest. 93:644 (which allowed for monitoring of alkaline phosphatase expression by flow cytometry)), high transduction frequencies can be achieved when the cells are exposed to vector on day 1, 2 or 3 after initiation of REM.

As described above, T cells prepared according to the invention can be used to restore, enhance, and/or modulate immunity in recipient individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, CD8+ CD4− cells are usually administered by infusion, with each infusion in a range of at least $10^6$ to $10^{10}$ cells/m$^2$, preferably in the range of at least $10^7$ to $10^9$ cells/m$^2$. The clones may be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphocytes and/or helper T lymphocytes) is readily achievable using the rapid expansion method of the present invention, as exemplified herein.

It has also been observed that T cells expanded using REM exhibited very high levels of transduction using vectors such as retroviral vectors which will be of great use in the contexts of cellular immunotherapy and gene therapy using lymphocytes.

The examples in Riddell et al., supra, exemplify the basic REM protocol (i.e. hp-REM), and also help to illustrate the general applications of REM technology to the preparation and use of expanded T cell populations and, in that regard, exemplify techniques and principles that can also be applied in the context of modified-REM.

The examples below illustrate exemplary modifications of the REM technology according to the present invention (i.e. modified-REM), to enable a reduction or elimination of the PBMC and/or EBV-LCL feeder cells that are characteristic of the hp-REM protocol.

All of the examples presented below are provided as a further guide to the practitioner of ordinary skill in the art, and are not to be construed as limiting the invention in any way.

EXAMPLES

Example 1
The Contribution of Monocyte Fc-γ Receptors in Rapid Expansion

The PBMC feeder cells, which are used in large excess to drive hp-REM, are a heterogeneous population of cells including B lymphocytes, T lymphocytes, monocytes, macrophages, and granulocytes, and Natural Killer ("NK") cells.

One of the activities believed to be supplied by PBMCs in the hp-REM protocol is the provision of Fc-γ receptors which can bind to the Fc portion of IgG antibody molecules. In particular, it is believed that T cell activation in the hp-REM protocol can be mediated by binding of Fc-γ receptors ("FcγR") on monocytes within the PBMC population to the Fc portion of anti-CD3 antibody (e.g. OKT3), which can thereby be "presented" by the monocytes to T cells within the population to be expanded. Following such activation, T cells are believed to be capable of initiating an "autocrine" growth stimulatory cycle in which activated T cells both secrete growth-stimulatory cytokines and also increase the expression of cell surface receptors for such cytokines. Supplying Fc-γ receptors, or otherwise effectively presenting anti-CD3 antibody, is thus believed to function in the initiation and promotion of T cell expansion.

Confirming and quantifying the contribution of monocyte Fc-γ receptors in the hp-REM protocol can be accomplished by depleting monocytes from the PBMC feeder cells.

Peripheral blood mononuclear cells can be obtained from any of a variety of sources, as described above. For the following examples, buffy coat layers (derived from healthy human donors) were obtained from a Red Cross blood bank. PBMCs were isolated using a Ficoll gradient, washed and stored in cell culture media (at 4 degrees Celsius) using standard techniques as referred to above.

A variety of techniques can be used for separating out various cell types from a mixed population such as PBMCs. By way of illustration, depletion of the monocyte/macrophage population was performed using sephadex G-10 chromatography (see, e.g., Section 3.6 in "Current Protocols in Immunology" (Wiley Interscience, 1992)). Monocyte depletion was monitored by flow cytometry following staining with FITC-conjugated anti-CD14 monoclonal antibody (available from, e.g., PharmaGen). CD14 expression before depletion was about 7.4% of total cells. Following depletion, it was about 1.5%.

In order to assess the impact of depleting monocytes on the ability of PBMCs to promote rapid expansion, a standard hp-REM protocol was used and monocyte-depleted PBMCs were compared with non-depleted PBMCs.

For purposes of illustration, a CTL line (designated "27EB") was prepared by procedures analogous to those described above. Briefly, PBMCs were obtained from an individual blood sample and were cultured with EBV-LCL derived from the same individual. After two weeks, CD8+ CTLs were isolated by "panning" with a flask coated with anti-CD8 antibodies (e.g. the AIS-CD8+ "CELLector flask" from Applied Immune Sciences).

For all of these illustrative examples, PBMCs were gamma-irradiated at 3600 rads (using a Cs-137 source) and EBV-LCL were irradiated at 10,000 rads.

Cultures were generally maintained as described above for hp-REM except that 10% fetal calf serum was used in place of human serum; and IL-2 was used at 25 units/ml and was generally first added on "day 0" (as opposed to 1 day after culture initiation), and then at 3–5 day intervals (generally, on day 5, and then again on day 8), as otherwise described above for the hp-REM protocol. OKT3 was generally used at about 10 ng/ml. Cells were typically harvested and quantified after 14 days of culture.

For this example, cultures were established with $5 \times 10^4$ CTL ("27EB", as described above), $5 \times 10^6$ irradiated EBV-LCL (i.e. a 100:1 excess over CTLs) (prepared and irradiated as described above), 10 ng/ml OKT3, 25 U/ml IL-2 and $2.5 \times 10^7$ irradiated PBMC (i.e. a 500:1 excess over CTLs) (either monocyte-depleted or nondepleted, prepared and irradiated as described above). Typical control cultures would include, for example, cultures without any added CTL. After 14 days of culture, cells were harvested and quantified.

In the case of the standard hp-REM protocol using nondepleted PBMCs, approximately $4.86 \times 10^7$ T cells were recovered, representing an expansion of approximately 882-fold.

As shown in TABLE 1, when monocyte-depleted PBMCs were used instead, only about $2.7 \times 10^7$ T cells were recovered, indicating that the expansion rate had dropped to about 55% of the control rate.

TABLE 1

| PBMC Cells | Method of depletion | T Cell Recovery | % Control T cell Expansion |
|---|---|---|---|
| Nondepleted PBMC | none | $4.86 \times 10^7$ | 100% |
| Monocyte-depleted PBMC | Sephadex column | $2.70 \times 10^7$ | 55% |

The above results provided further indication that monocytes within the PBMC population apparently contribute significantly to the ability of PBMCs to bring about the rapid expansion of T cells. In the following example, the ability to provide FcγR activity or its equivalent from a source other than PBMCs as a means for reducing the dependence of REM on large excesses of PBMC feeder cells.

Example 2
Replacement of Monocyte Fc-γ Receptor Activity in Modified-REM

As discussed above, Fc-γ receptors found on monocytes are believed to be responsible for a significant portion of the stimulatory activity supplied by PBMCs in the presence of antibodies such as anti-CD3 antibody (e.g. OKT3).

Having identified a stimulatory component supplied by the heterogeneous PBMC population, it is possible to reduce the dependence on PBMCs themselves by providing that activity (or its equivalent) from another source. Preferably, for use in modified-REM as described herein, the identified stimulatory activity will be provided by a mammalian cell line or as a non-cellular additive to the REM culture. Illustrative examples of both are provided below.

a. Use of Mammalian Cell Lines in Modified-REM

Cell lines expressing one of more identified T cell stimulatory activities provided by PBMCs (or LCL) can be effectively used to reduce the dependence of REM on such PBMC (or LCL) feeder cells. Where such a cell line is to be incorporated into the protocol, it is preferable, as described above, that the cell line not be a potential source of adventitious agents such as viruses. Accordingly, the supplemental cell line used is preferably not an EBV-transformed cell line (such as EBV-LCL). Also, for the rapid expansion of human T cells, it is generally preferable to use a cell line derived from a higher mammal, especially a primate, most preferably a human.

Mammalian cell lines expressing Fc-γ receptors have been described in the literature and can be obtained from a variety of sources. For example, a number of human tumor lines have been demonstrated to express Fc-γ receptors (see, e.g., R. J. Looney et al., J.Immunol.136:1641 (1986) (describing K562, an erythroleukemia cell line); S. J. Collins at el. 1977. Nature 270:347 (1977) (describing HL60, a promyelocytic cell line); C. Lozzio and B. Lozzio, Blood 45:321 (1975) (describing U937, a histiocytic lymphoma cell line); and G. R. Crabtree et al., Cancer Res. 38:4268 (1979).

Cell lines expressing Fc-γ receptors can also be readily prepared using standard molecular biological techniques. By way of illustration, FcγR-positive cell lines can be obtained by immortalizing cells that already express Fc-γ receptors using any of a variety of well-known techniques for transforming mammalian cells. Alternatively, an existing cell line such as a human cell line can be genetically modified to express Fc-γ receptors by introducing genes encoding Fc-γ receptors into the cells. Thus, a cell line of choice, such as a human cell line already expressing a stimulatory component such as a cytokine or a cell adhesion-accessory molecule (both of which are discussed below), can be further modified by introduction of genes encoding an FcγR.

By way of illustration, human monocytes apparently express two distinct Fc-γ receptor types ("FcγRI" and "FcγRII") which differ in their affinity for IgG antibody binding, (see, e.g., Ravetch and Kinet Annu. Review of Immunol. 9:457–492, 1991). In particular, FcγRI is generally a high affinity receptor ($K_a=10^8–10^9$) while FcγRII is generally a lower affinity receptor ($K_a=10^7$). The genes for both FcγRI and FcγRII have been identified and cloned. Previous studies have demonstrated that fibroblasts expressing the FcγRII receptor following gene transfer could effectively restore anti-CD3-dependent proliferation of monocyte-depleted T lymphocyte cultures (see, e.g., Peltz et al., J. Immunol. 141:1891 (1988)). Thus, a cell line genetically modified to express FcγR should be capable of supplying a significant portion of the stimulatory activity supplied by PBMCs in the hp-REM protocol. Use of such a cell line, potentially in conjunction with other components such as cytokines or adhesion-accessory molecules as described below, would thereby enable a decrease in the number of PBMCs required for rapid expansion.

b. Use of Non-cellular Additives for Modified-REM

In addition to providing T cell stimulatory components by way of a cell line, such as described above, it will be possible to provide a number of components (or their functional equivalents) as non-cellular additives to the modified-REM culture medium. Thus, as a different alternative to the FcγR activity apparently contributed by PBMC monocytes, it will be possible to provide a substitute or structural equivalent for FcγR activity. For example, an alternative means for achieving "presentation" of antibodies such as anti-CD3 antibodies to T cells is to conjugate such antibodies to beads (such as sephadex beads or magnetic beads).

In order to assess the ability of such bead-conjugated antibodies to substitute for soluble antibodies (which are presumably presented via FcγR), we conducted experiments to determine whether anti-CD3-conjugated magnetic beads can effectively replace soluble anti-CD3 monoclonal antibodies in the REM protocol.

Anti-CD3-conjugated magnetic beads ("BioMag anti-CD3") were obtained from Perceptive Diagnostics. The particles used were approximately 1 μm in size and had covalently attached anti-CD3 monoclonal antibodies loaded at approximately 20 μg antibody/$1\times10^7$ beads. A range of beads was chosen to approximate the number of antigen presenting cells ("APCs") estimated to be present within the PBMC population used in hp-REM.

For quantifying the actual impact on hp-REM, T cell expansion cultures containing $5\times10^4$ CTL, $5\times10^6$ irradiated EBV-LCL, $2.5\times10^7$ irradiated allogeneic PBMC and 25 U/ml IL-2 were established, essentially as described above in Example 1. Either 10 ng/ml of soluble anti-CD3 antibody (OKT3) or various quantities of anti-CD3-conjugated beads were added as the T cell activation reagent. Cell cultures were expanded and T cells counted, essentially as described for Example 1.

The results are shown in TABLE 2. While T cell expansion using anti-CD3-conjugated beads was somewhat less than with soluble OKT3 (in the range of about 80%), the results suggest that antibody-coated beads would be capable of inducing substantial levels of T cell activation/proliferation within a modified REM protocol. More detailed quantification of the relative role of anti-CD3 presentation as compared to other activities potentially provided by APCs within the PBMC population can be readily obtained by assessing the expansion rates obtainable with anti-CD3 beads using APC-depleted cultures, either in the presence or absence of various cytokines or other soluble stimulatory factors (which are described in more detail below).

TABLE 2

| Anti-CD3 source | T Cell Recovery | T Cell Expansion |
| --- | --- | --- |
| Soluble anti-CD3 Ab (OKT3) | $6.52 \times 10^7$ | 1304-fold |
| $1 \times 10^7$ BioMag anti-CD3 | $5.36 \times 10^7$ | 1071-fold |
| $5 \times 10^6$ BioMag anti-CD3 | $5.0 \times 10^7$ | 1000-fold |
| $2.5 \times 10^6$ BioMag anti-CD3 | $5.25 \times 10^7$ | 1051-fold |

Comparisons of the relative efficiency of providing various PBMC replacement components, as described herein, can be readily achieved by standard titration analyses in which the various components are added back at varying concentrations to a PBMC-limited REM culture (i.e. a culture in which PBMCs are included at a sub-optimal level). By way of illustration, experiments described below assessed the impact of adding various combinations of exogenous cytokines to sub-optimized hp-REM cultures in which the PBMC population had been reduced to one-half or one-quarter of an optimal starting level. Analogous assays can be readily performed for other components such as cells expressing FcγR or adhesion-accessory components, anti-CD3-conjugated beads, and/or other soluble stimulatory factors (such as monoclonal antibodies directed to T cell surface components), as described in more detail below.

Example 3
The Contribution of B Cells in Rapid Expansion

In order to quantify the contribution of B lymphocytes to the stimulus supplied by PBMCs, we examined the relative ability of B-cell-depleted PBMC populations to support REM.

Isolation of cells such as B cells (or other cells referred to herein) can be conveniently achieved using antibodies directed to a cell surface marker known to be present on the cells to be depleted. A variety of such markers are well known, including the various "CD" or "cluster of differentiation" markers; and antibodies to many such markers are readily obtainable. Also, for many such markers, beads conjugated with the antibodies are readily available and can greatly facilitate cell separation.

By way of illustration, CD 19 is a well-known cell surface marker for B lymphocytes. Magnetic beads that had been conjugated with anti-CD19 antibodies were obtained from Dynal, and were used to deplete a PBMC population of B cells, following standard procedures as described by the manufacturer.

Depletion was evaluated by fluorescence activated cell sorting ("FACS") after CD19 staining. The PBMC population was estimated to contain approximately 12% B cells prior to depletion and less than 1% B cells after depletion.

For testing the impact of B cell depletion on hp-REM, T cell expansion cultures containing $5 \times 10^4$ CTL, $5 \times 10^6$ irradiated EBV-LCL, $2.5 \times 10^7$ irradiated allogeneic PBMC (B-cell-depleted or nondepleted), 10 ng/ml OKT3 and 25 U/ml IL-2 were established; and, after 14 days, T cells were harvested and quantified as described above. The results, shown in TABLE 3, suggested that B cells also contribute to the stimulating activity supplied by PBMCs.

TABLE 3

| PBMC Cells | Method of depletion | T Cell Recovery | % Control T Cell Expansion |
|---|---|---|---|
| Nondepleted PBMC | none | $4.28 \times 10^7$ | 100% |
| B-cell-depleted PBMC | Anti-CD19 Magnetic Beads | $9.8 \times 10^7$ | 23% |

The decreased levels of T cell expansion in this and the preceding experiments suggests a role for monocytes and B cells as antigen presenting cells ("APCs") in the hp-REM protocol. (The inability to inhibit T cell expansion to the levels observed in Example 1 to the levels observed in this experiment may be a result of differences in cell depletion by the various methods used and/or the presence of small numbers of APC undetected by the assays used. It should also be noted that monocyte depletion as measured in Example 1 only reduced the monocyte population from about 7.5% to about 1.5%.)

There are a number of other well-known techniques that can be used to deplete various cell types from the PBMC population and that can therefore be used to provide additional confirmation and quantification of the results described herein. Thus, for example, nylon wool can be used to remove both monocytes and B cells (as well as any fibroblasts) from the PBMC population. The replacement of various APC activities in modified-REM is further described in the following example.

Example 4
Replacement of Various APC Activities in Modified-REM

The results obtained in the B-cell-depletion and monocyte-depletion experiments, described above, indicated that putative APCs in the PBMC population appear to contribute to the stimulus supplied by PBMCs. As described in Examples 1–2, the role of FcγR activity in presentation of anti-CD3 antibody is expected to account for some portion of the activity provided by putative APCs. Such FcγR activity can be supplied by another (non-PBMC) source, e.g. a cell line expressing FcγR or anti-CD3-conjugated beads, as also described above.

It is believed that APCs within the PBMC population also contribute adhesion-accessory molecules and stimulatory cytokines that would be expected to further enhance the activation/proliferation process. (Furthermore, as described below, T lymphocytes within the PBMC population are also expected to produce stimulatory cytokines as a result of activation via the anti-CD3 antibody.) The roles of such adhesion-accessory molecules and cytokines are described in more detail in the examples below.

Example 5
The Contribution of Cytokines in REM

Although anti-CD3 antibody (e.g. OKT3) is used to activate and induce the proliferation of T cell clones for their in vitro expansion, the γ-irradiated feeder PBMC population also contains a substantial population of T lymphocytes that are believed to be activatable by the anti-CD3 antibody. While such irradiated feeder cells are incapable of dividing, their activation via anti-CD3 antibody is believed to result in the secretion of multiple cytokines which can provide additional lympho-proliferative signals. For example, in addition to IL-2, anti-CD3 activation of T cells is believed to result in the secretion of other stimulatory cytokines including IL-1 α and β, IL-6, IL-8, GM-CSF, IFN-α and TNFα and β (du Moulin et. al. 1994. *Cytotechnology* 15:365). It is believed that the secretion of one or more of those cytokines can contribute substantially to the proliferative stimulus provided by PBMCs within the hp-REM protocol. Of the numerous other cytokines that have been characterized, a number of these are known to stimulate the growth of T cells, including, for example, IL-7 and IL-15. Others can be readily screened for their ability to enhance T cell proliferation and for their relative ability to reduce the dependence of REM on large numbers of PBMCs, as described herein.

By way of illustration, we analyzed the ability of a number of exogenously-supplied cytokines to reconstitute T cell expansion in REM cultures in which the numbers of PBMC feeder cells had been reduced to sub-optimal levels, in order to quantify the potential role of such cytokines in promoting REM.

Following procedures essentially analogous to those described above, cultures containing $5 \times 10^4$ CTL, $5 \times 10^6$ EBV-LCL, 10 ng/ml OKT3 and 25 U/ml IL-2 were established with either $2.5 \times 10^7$ irradiated PBMC (100% control), $1.25 \times 10^7$ irradiated PBMC (50%), or $6.12 \times 10^6$ irradiated PBMC (25%).

It is believed that a number of cytokines can act synergistically with IL-2 to promote T cell proliferation. In this illustrative experiment, the following exogenous cytokines were added to the cultures either alone or in various combinations as described: IL-1 (40 U/ml), IL-4 (200 U/ml), IL-6 (500 U/ml) and IL-12 (20 U/ml).

The results, shown in TABLE 4, confirmed that such cytokines can substantially enhance T cell expansion when PBMC populations are reduced to sub-optimal levels. It is not unexpected that expansion levels were not returned to that observed with the optimal number of PBMC feeders, because the PBMC population is believed to supply additional stimulatory activities as described herein. The data suggest that replacement of IL-4 with IL-12 in a cytokine cocktail may further enhance proliferation. The properties, sources, and DNA and protein sequences of many such cytokines are described in cytokine reference books such as "The Cytokine Facts Book" by R. Callard et al., supra. To take a single example for purposes of illustration, IL-12 is known to be a heterodimeric cytokine comprising two peptide chains (p35 and p40) that induces IFNγ production by T lymphocytes and co-stimulates the proliferation of peripheral blood lymphocytes. IL-12 also stimulates proliferation and differentiation of TH1 T lymphocytes, and is known to be produced by B cells, monocytes/macrophages, and B lymphoblastoid cells. The complete amino acid sequences for both the p35 and p40 chains are known and available on Genbank (Accession numbers provided in Callard). The IL-12 receptor has also been characterized (id.).

Additional cytokines and cocktails thereof can readily be tested in an analogous manner; and a comparison of stimulatory cocktails can then be made using even lower levels of PBMCs.

TABLE 4

| Added Cytokine(s) | PBMC | Cell Recovery | Expansion | Percent Control |
|---|---|---|---|---|
| IL-2 | $2.5 \times 10^7$ | $4.4 \times 10^7$ | 882-fold | 100% |
| IL-2 | $1.25 \times 10^7$ | $2.8 \times 10^7$ | 564-fold | 64% |
| IL-2 | $6.12 \times 10^6$ | $1.8 \times 10^7$ | 360-fold | 41% |
| IL-2 + IL-1 | $1.25 \times 10^7$ | $3.2 \times 10^7$ | 648-fold | 73% |
| IL-2 + IL-1 | $6.12 \times 10^6$ | $2.4 \times 10^7$ | 486-fold | 55% |
| IL-2 + IL-4 | $1.25 \times 10^7$ | $2.0 \times 10^7$ | 402-fold | 46% |
| IL-2 + IL-4 | $6.12 \times 10^6$ | $1.5 \times 10^7$ | 295-fold | 33% |
| IL-2 + IL-6 | $1.25 \times 10^7$ | $3.2 \times 10^7$ | 636-fold | 72% |
| IL-2 + IL-6 | $6.12 \times 10^6$ | $3.0 \times 10^7$ | 606-fold | 69% |
| IL-2 + IL-12 | $1.25 \times 10^7$ | $4.65 \times 10^7$ | 930-fold | 105% |
| IL-2 + IL-12 | $6.12 \times 10^6$ | $2.88 \times 10^7$ | 558-fold | 63% |
| IL-2 + IL-1 + IL-4 + IL-6 | $1.25 \times 10^7$ | $3.8 \times 10^7$ | 768-fold | 87% |
| IL-2 + IL-1 + IL-4 + IL-6 | $6.12 \times 10^6$ | $3.1 \times 10^7$ | 618-fold | 70% |

Further evidence that soluble components of the feeder cell supernatant can provide an effective stimulus for low-PBMC REM was obtained by reducing the PBMC population to sub-optimal levels and using a REM supernatant to provide soluble stimulatory signals.

Briefly, a standard hp-REM protocol was performed as described above, using an antigen-specific CTL clone and performing a 48-hour REM expansion with PBMC (500:1), EBV-LCL (100:1), anti-CD3 antibody (10 ng/ml), and recombinant human IL-2 (25 units/ml). After 48 hours, the cells were harvested and the supernatant ("REM supernatant") was examined as a source of soluble stimulatory factors in a REM expansion in which PBMC were reduced to sub-optimal levels (i.e. ½, ¼ or ⅛ of optimal or "SOP").

The results, as shown in TABLE 5, confirm that such soluble factors can provide an effective stimulatory signal in the context of low-PBMC REM. In particular, a large proportion of the reduction in fold proliferation levels observed when PBMC are reduced can be overcome by using the REM supernatant in place of the standard medium. In addition, the more the PBMC were reduced (i.e. to ⅛ of optimum), the greater was the observed effect from using the REM supernatant (1022-fold average expansion using the REM supernatant versus 359-fold expansion without). Such supernatants and/or their components such as individual cytokines or "cocktails" thereof can thus be used to reduce the need for conducting REM with large excesses of feeder cells such as PBMCs).

TABLE 5

| Medium | PBMC | Avg. Fold Proliferation | Std. Dev. |
|---|---|---|---|
| SOP MEDIUM | SOP | 1255 | ±160 |
|  | 1/2 SOP | 1178 | ±64 |
|  | 1/4 SOP | 996 | ±23 |
|  | 1/8 SOP | 359 | ±29 |
| 48 HR. REM SUP. | SOP | 1253 | ±144 |
|  | 1/2 SOP | 1218 | ±73 |
|  | 1/4 SOP | 1178 | ±89 |
|  | 1/8 SOP | 1022 | ±77 |

Example 6
Replacement of Cytokine Activity in Modified-REM

As described above, a large number of cytokines have been described and are widely available, including a number of cytokines that are known to stimulate T lymphocytes. As will be apparent to those of skill in the art, such cytokines (whether or not they were previously known to stimulate T cells) can be readily tested for their ability to augment rapid expansion using methods such as those above. In addition, for any of the rapid expansion techniques described herein, the resulting expanded T cells can be monitored for the maintenance of various desired characteristics, using methods such as those illustrated above for hp-REM.

Cytokines to be used in modified-REM can be introduced to the target T cells in any of several ways as illustrated herein. Thus, for example, one or more cytokines can be added to the medium, as exemplified above. Alternatively, or in addition, cytokines can also be supplied by cells secreting the cytokines into the REM medium. Thus, by way of illustration, a mammalian cell line known to secrete a particular cytokine or combination of cytokines can be used. Alternatively, a mammalian cell line that does not already secrete a particular cytokine (or that secretes it at suboptimal levels) can be readily modified by introducing a gene encoding the desired cytokine. As is well known, the gene can be placed under the control of any of a variety of promoters (as alternatives to its original promoter) so that expression of the cytokine can be controlled to maximize its effectiveness. The entire sequences for a large number of cytokines are known and encoding DNA is often available. Many such sequences are published in nucleic acid and/or protein databases (such as GenEMBL, GENBANK or Swissprot); see, e.g., the Cytokine Facts Book, R. E. Callard et al., Academic Press, 1994). Also, as described above, such additional mammalian cell lines can be modified to provide several T cell stimulatory activities at once.

Example 7
The Role of Accessory-Adhesion Molecules in Rapid Expansion

As discussed above, APCs such as monocytes and B cells also provide other T cell co-stimulatory signals which serve to enhance T cell activation/proliferation. Thus, while T cell activation involves the specific recognition of MHC-bound antigenic peptides on the surface of APCs (which interact with the T cell receptor/CD3 complex), a number of antigen-non-specific receptor:ligand interactions between APCs and T cells can further enhance T cell activation/proliferation. In particular, APCs express ligands for a variety of receptors on T cells, and it appears that T cell activation/proliferation is the result of a combination of signals delivered through the T cell receptor and other signaling molecules. A number of such receptor:ligand interactions have already been identified and, for a number of those, inhibition of the receptor:ligand interactions have been reported to inhibit T cell proliferation and cytokine secretion. By way of illustration, a number of receptor:ligand pairs that are considered likely to play a role in T cell activation/proliferation are listed in TABLE 6 below.

TABLE 6

| Receptor (T cell) | Ligand (APC) |
|---|---|
| CD4 | Class II MHC |
| CD8 | Class I MHC |
| CD11a (LFA-1) | CD54 (ICAM-1) and ICAM 2 & 3 |
| CD2 | CD58 (LFA-3) |
| CD5 | CD72 |

TABLE 6-continued

| Receptor (T cell) | Ligand (APC) |
| --- | --- |
| CD49d (VLA-4) | fibronectin (FN) |
| CD27 | ligand to CD27 |
| CD28 | CD80 (B7.1) and CD86 (B7.2) |
| CD44 | hyaluronate |

While many of these molecules have been reported to function in adhesion (enhancing cell:cell and/or cell:substrate interactions), many have also been shown to deliver T cell co-stimulatory signals such as enhancing intracellular calcium and the activation of PI and PKC (see, e.g., Geppert et al. 1990. Immunol. Reviews 117:5–66).

The interactions of such adhesion-accessory molecules as described above have been shown to positively enhance activation of resting T lymphocytes. Antibodies which bind these accessory molecules have been shown, under specific conditions, to provide T cell activation signals (see, e.g., the references cited below). Also, the addition of purified accessory molecule ligands ICAM-1 and LFA-3 (ligands for CD11a and CD2 respectively) to purified T cells being stimulated with anti-CD3 monoclonal antibody has been shown to provide co-stimulatory signals for T cell activation and proliferation (see, e.g., Semnani et al. 1994. J. Exp. Med. 180:2125).

Thus, various antibodies directed against CD4 and CD8 are capable of either inhibiting T cell activation (see, e.g., I. Bank and L. Chess. 1985. J. Exp. Med. 162:1194; G. A. van Seventer. 1986. Eur. J. Immunol. 16:1363) or synergizing with anti-CD3 mAb to induce T cell proliferation (see, e.g., F. Emmrich et al. 1986. PNAS 83:8298; T. Owens et al. 1987. PNAS 84:9209; K. Saizawa et al. 1987. Nature 328:260). As is well known by those of skill in the art, a collection of antibodies raised against a particular antigen would be expected to contain antibodies binding to a variety of different sites on the antigen.

A number of studies have shown that antibodies to other adhesion-accessory molecules are capable of augmenting T cell stimulation/proliferation. By way of illustration, see, e.g., J. A. Ledbetter et al. 1985. J. Immunol 135:2331 (antibodies directed to CD5 and CD28 augment anti-CD3-induced T cell proliferation); P. J. Martin et al. 1986. J. Immunol. 136:3282 (antibodies to CD28 augment anti-CD3-induced T cell proliferation); R. Galandrini et al. 1993. J. Immunol. 150:4225, and Y. Shimizu. 1989. J. Immunol 143:2457 (antibodies directed against CD44 augment anti-CD3 induced T cell proliferation); S. C. Meur et al. 1984. Cell 36:897 (antibodies directed against the T11.2 and T11.3 epitopes of CD2 stimulate T cell proliferation); R. van Lier. 1987. J. Immunol. 139:1589 (antibodies directed against CD27 augment anti-CD3-induced T cell proliferation); Bossy et al. 1995. Eur. J. Immunol. 25:459 (antibodies to CD50 (ICAM-3) augment anti-CD3-induced T cell proliferation); M. C. Wacholtz et al. 1989. J. Exp. Med. 170:431 (antibodies directed to LFA-1 augment anti-CD3-induced proliferation when the two antibodies are crosslinked on the T cell surface); G. A. van Seventer et. al. 1990. J. Immunol. 144:4579 (purified ICAM-1 immobilized on plastic with anti-CD3 mAb co-stimulates T cell proliferation via the LFA-1 molecule); Y. Shimizu et al. 1990. J. Immunol 145:59 (purified fibronectin on plastic with anti-CD3 mAb co-stimulates T cell proliferation, and antibodies to VLA4 and VLA5 inhibited this activity indicating the role of VLA4 and VLA5 as co-stimulatory T cell receptors); N. K. Damle et al. 1992. J. Immunol. 148:1985 (soluble ICAM-1, B7-1, LFA-3 and VCAM augment anti-CD3-induced T cell proliferation). Quantification of the relative contribution of such adhesion-accessory factors within the REM protocol can be readily accomplished using deletion techniques and titration experiments in PBMC-limited hp-REM assays analogous to those illustrated above for the combinations of various cytokines.

Example 8

Replacement of Adhesion-Accessory Molecule Activity in Modified-REM

In an analogous manner to the modifications described above, and perhaps in combination with such modifications, the REM protocol can thus be modified to include a characterized cell line expressing high levels of these receptor ligands (obtained by, e.g., gene modification of a cell line of choice or by the identification of established cell lines already expressing such molecules). It is also possible to utilize antibodies directed against accessory molecules known to induce signal transduction and/or to use purified accessory ligand molecules as means of substituting for the corresponding activity provided by the PBMC feeder cells, thereby enabling a reduction in the number of PBMCs required to drive REM.

Example 9

Replacement of Additional Stimulatory Activities Provided by EBV-LCL

While EBV-LCL do not appear to be sufficient for achieving maximal T cell expansion, they are capable of augmenting expansion in the hp-REM protocol. Analysis of EBV-LCL has indicated that they express adhesion molecules such as LFA-1, ICAM-1, and LFA-3, as well as FcγR. In addition, EBV-LCL secrete IL-1 (Liu et al. Cell. Immunol, 108:64–75, 1987) and IL-12 (Kobayashi et al., 1989. J. Exp. Med. 170:827), both of which are also secreted by APCs.

As described above, it is believed that such components can be readily supplied by other sources—thereby reducing the need for the large numbers of PBMC and/or EBV-LCL feeder cells characteristic of hp-REM.

Example 10

The use of anti-CD21 Antibody in Modified REM

CD21 is an accessory molecule expressed on mature B lymphocytes and, at low levels, on T lymphocytes. We examined the ability of a molecule that binds to CD21 to provide a stimulatory signal in the context of modified REM.

In a first set of experiments, we used plate-bound anti-CD21 antibody to examine the ability to provide a stimulatory signal in modified REM in which the EBV-LCL feeder population was completely eliminated. Two different antigen-specific CTL clones ("R7" which is alloantigen-specific, and "11E2" which is EBV-specific) were tested in a modified REM procedure in which EBV-LCL were eliminated, but other components were maintained as described above (PBMC at 500:1, IL-2 at 25 units/ml). Anti-CD21 antibodies are available from commercial sources. We used the anti-CD21 antibody available from Pharmingen. Anti-CD3 antibody was also used, and was bound to plates, as with anti-CD21. Cultures were expanded over a two week standard REM cycle, essentially as described above.

The data, as shown in TABLE 7, revealed that the inclusion of anti-CD21 antibody resulted in a large increase in the fold proliferation obtainable without the use of EBV-LCL (to 650% of control and 408% of control for R7 and 11E2, respectively).

A second set of experiments, performed using soluble anti-CD21 antibody, provided additional confirmatory data.

In particular, a range of anti-CD21 concentrations was used in REM as above, except that both anti-CD21 and anti-CD3 were supplied as soluble antibodies (anti-CD21 at concentrations ranging from 0 ng/ml to 1.75 ng/ml; anti-CD3 at 10 ng/ml).

As shown in TABLE 8, the removal of all EBV-LCL feeder cells from the cultures resulted in a substantial reduction in the average fold proliferation (to 10% of control and 14% of control for R7 and 11E2, respectively). The addition of even small amounts of anti-CD21 antibody to the culture media resulted in a large increase in fold proliferation (to 72% of control and 57% of control for R7 and 11E2, respectively).

While anti-CD21 antibody provides a convineinet method for enhancing the stimulatory signal, it is also possible to stimulate CD21 in other ways. For example, in addition to anti-CD21 antibody, other molecules that can be used to bind to CD21 include C3d, C3dg, iC3b and gp350/220 of EBV (see, e.g., W. Timens et al., pages 516–518 in "Leucocyte Typing V, White Cell Differentiation Antigens," Schlossman, S. F., et al. (eds.), Oxford University Press, Oxford, 1995). Also, as described above, while such T cell stimulatory components can be provided as soluble factors in the modified REM medium, they can also be provided by a cell line included in the medium (e.g., a cell line that secretes or presents a molecule that binds to CD21).

TABLE 7

| Clone | Specificity | Stimulation | Fold Proliferation | % Control |
|---|---|---|---|---|
| R7 | Alloantigen | anti-CD3 | 96 | 100% |
| | | anti-CD3 + anti-CD21 | 624 | 650% |
| 11E2 | EBV | anti-CD3 | 48 | 100% |
| | | anti-CD3 + anti-CD21 | 196 | 408% |

TABLE 8

| Clone | Condition | Fold Proliferation | % Control |
|---|---|---|---|
| R7 | SOP REM | 900 | 100% |
| | 1.75 ng/ml anti-CD21 | 228 | 25% |
| | 1.25 ng/ml anti-CD21 | 156 | 17% |
| | 0.625 ng/ml anti-CD21 | 516 | 57% |
| | 0.325 ng/ml anti-CD21 | 372 | 41% |
| | 0 ng/ml anti-CD21 | 90 | 10% |
| 11E2 | SOP REM | 420 | 100% |
| | 1.75 ng/ml anti-CD21 | 96 | 24% |
| | 1.25 ng/ml anti-CD21 | 192 | 48% |
| | 0.625 ng/ml anti-CD21 | 288 | 72% |
| | 0.325 ng/ml anti-CD21 | 132 | 33% |
| | 0 ng/ml anti-CD21 | 60 | 14% |

What is claimed is:

1. A method for expanding an initial T lymphocyte population in culture medium in vitro, comprising the steps of:

adding an initial T lymphocyte population to a culture medium in vitro;

adding to the culture medium a non-dividing mammalian cell line expressing at least one T-cell-stimulatory component selected from the group consisting of an Fc-γ receptor, a cell adhesion-accessory molecule, a molecule that binds CD21, and a cytokine, wherein said cell line is not an EBV-transformed lymphoblastoid cell line (LCL);

adding IL-2 to the culture medium, wherein the concentration of IL-2 is at least 10 units/ml; and incubating the culture, thereby expanding the T lymphocyte population.

2. The expansion method of claim 1, further comprising the step of adding anti-CD3 monoclonal antibody to the culture medium wherein the concentration of anti-CD3 monoclonal antibody is at least 1.0 ng/ml.

3. The expansion method of claim 1, wherein said mammalian cell line comprises at least one cell type that is present at a frequency at least three times that found in human peripheral blood mononuclear cells (human PBMCs).

4. The expansion method of claim 1, wherein said T-cell-stimulatory component is an Fc-γ receptor.

5. The expansion method of claim 1, wherein said T-cell-stimulatory component is a cell adhesion-accessory molecule.

6. The expansion method of claim 1, wherein said T-cell-stimulatory component is a cytokine.

7. The expansion method of claim 5, wherein said cell adhesion-accessory molecule is selected from the group consisting of Class II MHC, Class I MHC, ICAM 1, ICAM 2, ICAM 3, CD58, CD72, fibronectin, CD80, CD86, hyaluronate, and CD27 ligand.

8. The expansion method of claim 1, wherein said T-cell-stimulatory component is a molecule that binds to CD21.

9. The expansion method of claim 6, wherein said cytokine is selected from the group consisting of IL-1, IL-2, IL-4, IL-6, IL-7, IL-12 and IL-15.

10. The expansion method of claim 1, further comprising the step of adding a soluble T-cell-stimulatory factor to the culture medium.

11. The expansion method of claim 10, wherein said soluble T-cell-stimulatory factor is selected from the group consisting of a cytokine, an antibody specific for a T cell surface component, and an antibody specific for a component capable of binding to a T cell surface component.

12. The expansion method of claim 11, wherein said soluble T-cell-stimulatory factor is a cytokine selected from the group consisting of IL-1, IL-2, IL-4, IL-6, IL-7, IL-12 and IL-15.

13. The expansion method of claim 11, wherein said soluble T-cell-stimulatory factor is an antibody specific for a T cell surface component, and wherein said T cell surface component is selected from the group consisting of CD4, CD8, CD11a, CD2, CD5, CD49d, CD27, CD28 and CD44.

14. The expansion method of claim 11, wherein said soluble T-cell-stimulatory factor is an antibody specific for a component capable of binding to a T cell surface component, and wherein said T cell surface component is selected from the group consisting of CD4, CD8, CD11a, CD2, CD5, CD49d, CD27, CD28 and CD44.

15. The expansion method of claim 10, wherein said soluble T-cell-stimulatory factor is a molecule that binds to CD21.

16. The expansion method of claim 15, wherein said molecule that binds to CD21 is an anti-CD21 antibody.

17. The expansion method of claim 1, further comprising the step of adding to the culture a multiplicity of peripheral blood mononuclear cells (PBMCs).

18. The expansion method of claim 17, wherein the ratio of PBMCs to initial T cells to be expanded is less than 40:1.

19. The expansion method of claim 17, wherein the ratio of PBMCs to initial T cells to be expanded is less than 10:1.

20. The expansion method of claim 17, wherein the ratio of PBMCs to initial T cells to be expanded is less than 3:1.

21. The expansion method of claim 1, further comprising the step of adding to the culture a multiplicity of EBV-transformed lymphoblastoid cells (LCLs).

22. The expansion method of claim 21, wherein the ratio of LCLs to initial T cells to be expanded is less than 10:1.

23. The expansion method of claim 1, wherein the initial T lymphocyte population comprises at least one human CD8+antigen-specific cytotoxic T lymphocyte (CTL).

24. The expansion method of claim 1, wherein the initial T lymphocyte population comprises at least one human CD4+antigen-specific helper T lymphocyte.

25. A method for rapidly expanding an initial T lymphocyte population in culture medium in vitro, comprising the steps of:

adding an initial T lymphocyte population to a culture medium in vitro;

adding to the culture medium a molecule that binds to CD21; and incubating the culture, thereby expanding the T lymphocyte population.

26. The method of claim 25, wherein said molecule that binds to CD21 is an anti-CD21 antibody.

* * * * *